US012653404B2

(12) United States Patent
Clingman et al.

(10) Patent No.: US 12,653,404 B2
(45) Date of Patent: *Jun. 16, 2026

(54) OPTOACOUSTIC IMAGE ANALYSIS METHOD AND SYSTEM FOR AUTOMATICALLY ESTIMATING LESION TRAITS

(71) Applicant: Seno Medical Instruments, Inc., San Antonio, TX (US)

(72) Inventors: Bryan Clingman, San Antonio, TX (US); Sandra G. Dykes, Boerne, TX (US)

(73) Assignee: Seno Medical Instruments, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/944,152

(22) Filed: Nov. 12, 2024

(65) Prior Publication Data

US 2025/0127403 A1 Apr. 24, 2025

Related U.S. Application Data

(63) Continuation of application No. 16/445,765, filed on Jun. 19, 2019, now Pat. No. 12,178,549.
(Continued)

(51) Int. Cl.
| | |
|---|---|
| *A61B 5/00* | (2006.01) |
| *G06F 18/2411* | (2023.01) |
| *G06F 18/2413* | (2023.01) |
| *G06F 18/2415* | (2023.01) |
| *G06N 20/00* | (2019.01) |
| *G06N 20/10* | (2019.01) |
| *G06N 20/20* | (2019.01) |
(Continued)

(52) U.S. Cl.
CPC .......... *A61B 5/0095* (2013.01); *A61B 5/4312* (2013.01); *A61B 5/4887* (2013.01); *A61B 5/7267* (2013.01); *A61B 5/7275* (2013.01); *G06F 18/2411* (2023.01); *G06F 18/24147* (2023.01); *G06F 18/24155* (2023.01); *G06N 20/00* (2019.01); *G06N 20/10* (2019.01); *G06N 20/20* (2019.01); *G06V 10/764* (2022.01); *G16H 50/20* (2018.01); *G16H 50/30* (2018.01); *G06V 2201/03* (2022.01); *G16H 50/70* (2018.01)

(58) Field of Classification Search
CPC ... A61B 5/0095; A61B 5/7264; A61B 5/7267; G06L 2207/22081; G06L 2207/22084; G01N 29/4481
See application file for complete search history.

(56) References Cited

U.S. PATENT DOCUMENTS

| | | | | |
|---|---|---|---|---|
| 10,993,653 | B1 * | 5/2021 | Thomas | .................... A61B 8/48 |
| 2014/0301619 | A1 * | 10/2014 | Stavros | ................ A61B 5/0035 |
| | | | | 382/131 |

OTHER PUBLICATIONS

Office Action for corresponding CN Application No. 201980076919 dated Jan. 13, 2025 (25 pages).

* cited by examiner

*Primary Examiner* — Nyrobi Celestine

(74) *Attorney, Agent, or Firm* — Dean D. Small; Carroll, Hoette & Butscher, LLC

(57) ABSTRACT

A system and method for performing optoacoustic classification prediction is provided. The method utilizes one or more processors in connection with receiving OA feature scores in connection with OA images collected from a patient examination for a volume of interest. The volume of interest includes a lesion. The method applies the OA feature
(Continued)

scores to a classification model to obtain a predictive result indicative of a trait of the lesion.

14 Claims, 10 Drawing Sheets

Related U.S. Application Data

(60) Provisional application No. 62/744,606, filed on Oct. 11, 2018.

(51) Int. Cl.

| | | |
|---|---|---|
| *G06V 10/764* | (2022.01) | |
| *G16H 50/20* | (2018.01) | |
| *G16H 50/30* | (2018.01) | |
| *G16H 50/70* | (2018.01) | |

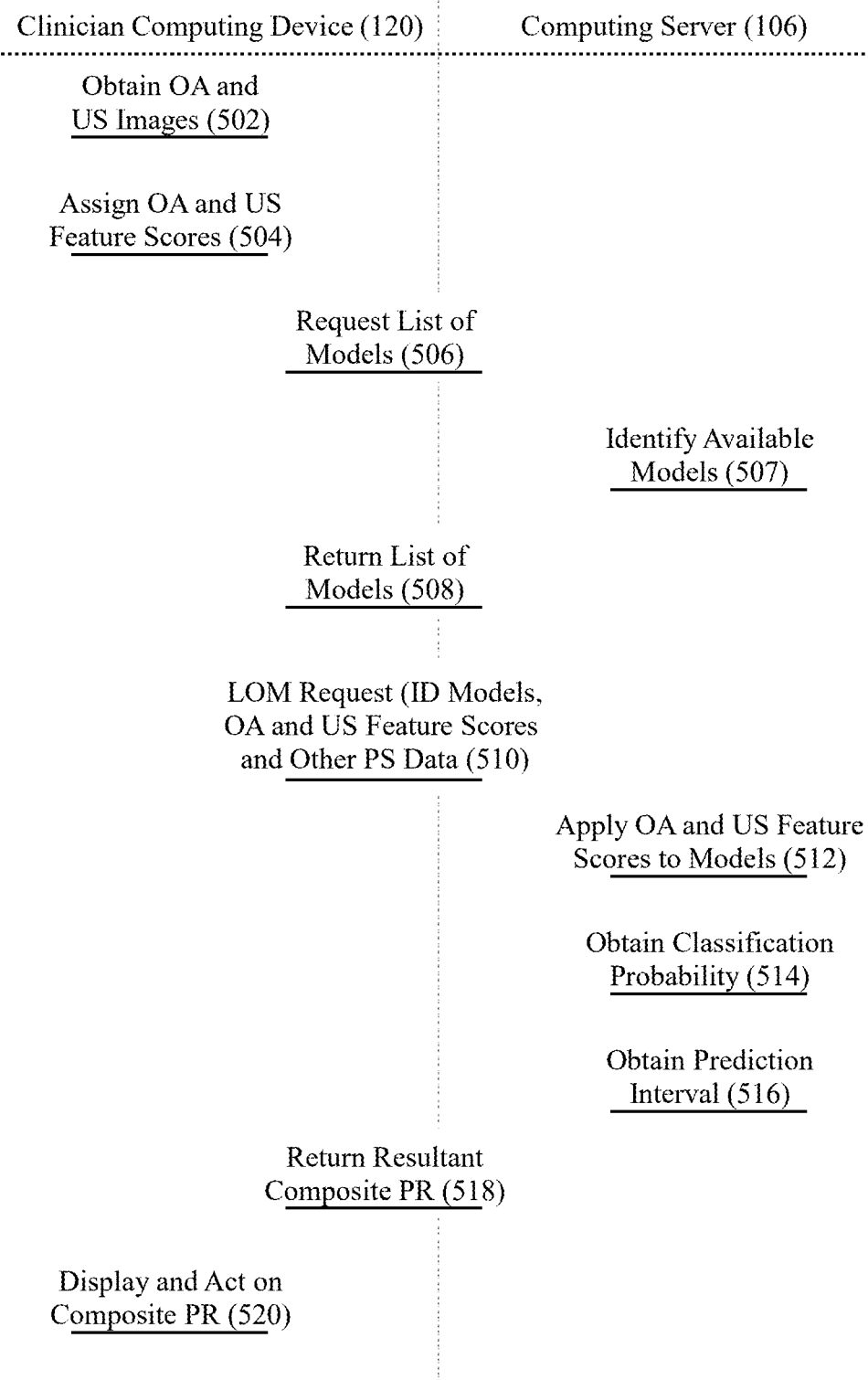

Clinician Computing Device (120)          Computing Server (106)

Obtain OA and
US Images (502)

Assign OA and US
Feature Scores (504)

Request List of
Models (506)

Identify Available
Models (507)

Return List of
Models (508)

LOM Request (ID Models,
OA and US Feature Scores
and Other PS Data (510)

Apply OA and US Feature
Scores to Models (512)

Obtain Classification
Probability (514)

Obtain Prediction
Interval (516)

Return Resultant
Composite PR (518)

Display and Act on
Composite PR (520)

Figure 5A

OPTOACOUSTIC IMAGE ANALYSIS METHOD AND SYSTEM FOR AUTOMATICALLY ESTIMATING LESION TRAITS

CROSS REFERENCE TO RELATED APPLICATIONS

This application is a continuation of, and claims priority, to U.S. application Ser. No. 16/445,765, filed 19 Jun. 2019, which claims priority to U.S. Provisional Application No. 62/744,606, filed 11 Oct. 2018 the subject matter of which are herein incorporated by reference in their entirety.

BACKGROUND

Embodiments herein generally relate to optoacoustic (OA) imaging methods.

Worldwide, breast cancer is the most commonly diagnosed cancer, and the second leading cause of cancer death in women. Although the death rate from breast cancer has significantly decreased in the last 20 years, breast cancer is still one of the major causes of morbidity and mortality in western women.

Ultrasound is used today in the evaluation of suspicious breast masses, and guiding biopsies. However, tissue architecture non-invasively assessed by breast ultrasound imaging does not provide enough prognostic information about cancers, and therefore has limited value to clinicians beyond the assessment of tumor size and morphology.

A need remains for improvements in optimal acoustic image analysis.

SUMMARY

In accordance with embodiments herein, a method for performing optoacoustic classification prediction is provided. The method utilizes one or more processors in connection with receiving OA feature scores in connection with OA images collected from a patient examination for a volume of interest. The volume of interest includes a lesion. The method applies the OA feature scores to a classification model to obtain a predictive result indicative of a trait of the lesion and outputs the predictive result.

Optionally, the method may receive non-OA feature scores in connection with non-OA images collected from the patient examination for the volume of interest. The method may apply the non-OA feature scores, in combination with the OA feature scores, to the classification model to obtain the predictive result. The predictive result may be i) indicative of a likelihood that the lesion may be in a malignant class or benign class, ii) indicative of a care path decision and/or iii) a likelihood of malignancy (LOM) designator that the lesion may be in the malignant class or benign class. The LOM designator may represent a mean confidence interval. The predictive result may further comprise a confidence interval range. The applying operation may comprise applying the OA feature scores to an ensemble of classification model. At least a portion of the classification models may output a corresponding predictive result.

Optionally, the method may further comprise combining the predictive results to form a composite predictive result indicative of the likelihood that the lesion may be in the malignant class. The classification models may represent decision trees that may comprise decision points, branches and lesion traits. The applying operation may comprise testing the OA feature scores at the decision points and may branch through the decision trees based on the testing until reaching one of the lesion traits. The classification model may be built utilizing a predictive machine learning classifier and a labeled data set that may include OA feature scores and malignant or benign labels for lesion in the data set.

In accordance with embodiments herein, a method for building a classification model in connection with optoacoustic (OA) classification prediction is provided. The method utilizes one or more processors in connection with receiving a labeled data set for multiple patients. The labeled data set includes OA feature scores for lesions in OA images of volumes of interest from examinations for the multiple patients. The labeled data set includes class designators indicating a trait of the lesion. The method utilizes a predictive machine learning (PML) classifier to build an ensemble of classification models based on the labeled data set. Each of the classification models includes predictive results indicative of the trait of the lesion.

Optionally, the labeled data set may include a combination of i) the OA feature scores for OA images from examinations of the multiple patients ii) the class designator that has been determined and recorded with the OA feature scores, and iii) non-OA feature scores for non-OA images from examinations of the multiple patient. The PML classifier may include one or more of classification and regression trees (CART), C4.5 decision trees, K nearest-neighbor, Support Vector Machines (SVM), and Naïve Bayes classifiers. The PML classifier may utilize a random forest algorithm to form an ensemble of decision trees corresponding to the classification models. The PML classifier may utilize an extreme gradient boosting algorithm, in combination with classification and regression trees (CART) decision trees to form the classification models. The classification models may represent decision trees that comprise decision points, branches and lesion traits.

In accordance with embodiments herein, a system for performing optoacoustic classification prediction is provided. The system comprises memory configured to store program instructions. One or more processors are provided that, when executing the program instructions, are configured to receive OA feature scores in connection with OA images collected from a patient examination for a volume of interest, the volume of interest including a lesion, apply the OA feature scores to a classification model to obtain a predictive result indicative of a likelihood that the lesion is in a malignant class or benign class and output the predictive result.

Optionally, the one or more processors may be further configured to receive non-OA feature scores in connection with non-OA images collected from the patient examination for the volume of interest. The system may apply the non-OA feature scores, in combination with the OA feature scores, to the classification model to obtain the predictive result. The predictive result may comprise a likelihood of malignancy (LOM) designator that the lesion may be in the malignant class or benign class. The LOM designator may represent a mean confidence interval. The predictive result may further comprise a confidence interval range. The one or more processors may be further configured to apply the OA feature scores to an ensemble of classification models. At least a portion of the classification models may output a corresponding predictive result.

Optionally, the processors may be further configured to combine the predictive results to form a composite predictive result indicative of the likelihood that the lesion may be in the malignant class. The classification models may represent decision trees that comprise decision points, branches and lesion traits. The applying operation may comprise testing the OA feature scores at the decision points and may branch through the decision trees based on the testing until reaching one of the lesion traits. The classification model may be built utilizing a predictive machine learning classifier and a labeled data set that may include OA feature scores and malignant or benign labels for lesion in the data set.

In accordance with embodiments herein, a system for building a classification model in connection with Opto acoustic (OA) classification prediction is provided. The system comprises memory configured to store program instructions. One or more processors are provided that, when executing the program instructions, or configured to receive a labeled data set for multiple patients. The labeled data set includes OA feature scores for lesions in OA images of volumes of interest from examinations for the multiple patients. The labeled data set include class designators indicating whether the lesions are in a benign class or malignant class. The system utilizes a predictive machine learning (PML) classifier to build an ensemble of classification models based on the labeled data set. Each of the classification models includes predictive results indicative of a likelihood that a lesion is in a malignant class or benign class.

Optionally, the labeled data set may include a combination of i) the OA feature scores for OA images from examinations of the multiple patients ii) the class designator that has been determined and recorded with the OA feature scores, and iii) non-OA feature scores for non-OA images from examinations of the multiple patient. The PML classifier may include one or more of classification and regression trees (CART), C4.5 decision trees, K nearest-neighbor, Support Vector Machines (SVM), and Naïve Bayes classifiers. The PML classifier may utilize a random forest algorithm to form an ensemble of decision trees corresponding to the classification models. The PML classifier may utilize an extreme gradient boosting algorithm, in combination with classification and regression trees (CART) decision trees to form the classification models. The classification models may represent decision trees that comprise decision points, branches and lesion traits.

BRIEF DESCRIPTION OF THE DRAWINGS

FIG. 5A illustrates a distributed operation diagram to further describe operations performed by a clinician computing device and a computing server in accordance with embodiments herein.

DETAILED DESCRIPTION

Figure 1:
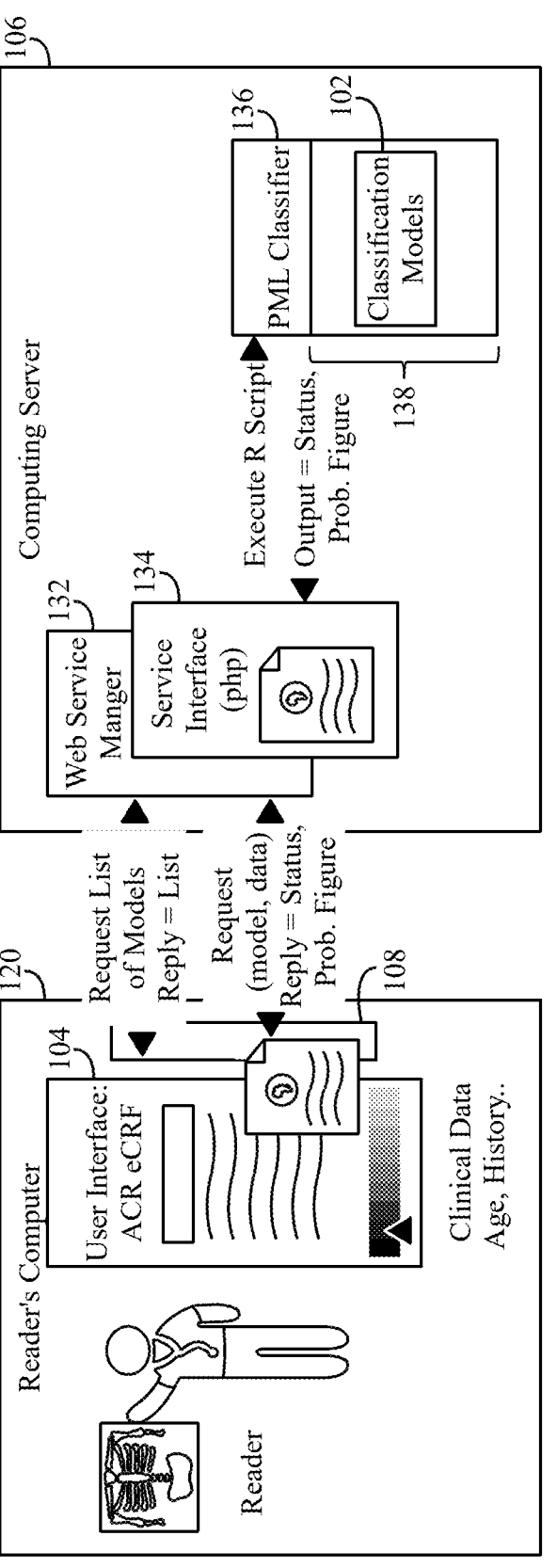
FIG. 1 illustrates a block diagram of the basic components of a PML classification system in accordance with embodiments herein.

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The systems and methods are described below with reference to, among other things, block diagrams, operational illustrations and algorithms of methods and devices to provide optoacoustic imaging with out-of-plane artifact suppression. It is understood that each block of the block diagrams, operational illustrations and algorithms and combinations of blocks in the block diagrams, operational illustrations and algorithms, can be implemented by means of analog or digital hardware and computer program instructions.

These computer program instructions can be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some cases frequency domain based algorithms require zero or symmetric padding for performance. This padding is not essential to describe the embodiment of the algorithm so it is sometimes omitted from the description of the processing steps. In some cases, where padded is disclosed in the steps, the algorithm may still be carried out without the padding. In some cases padding is essential, however, and cannot be removed without corrupting the data.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying Figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

Related Publications, Applications & Patents

Embodiments herein may be implemented in connection with one or more of the systems and methods described in one or more of the following patents, publications and/or published applications, all of which are expressly incorporated herein by reference in their entireties:

U.S. Provisional Application 62/725,632, titled "Qualitative Optoacoustic Imaging (OA/US) Features of Breast Cancers Correlated with Molecular Subtypes", filed Aug. 31, 2018;

U.S. Pat. No. 7,999,161, titled "Laser-Activated Nanothermolysis Of Cells" filed Jul. 23, 2007;

U.S. Pat. No. 9,289,191, titled "System and method for Acquiring Optoacoustic Data and Producing Parametric Maps Thereof", and filed Jun. 13, 2012;

U.S. Pat. No. 9,517,055, titled "System And Method For Acquiring Optoacoustic Data And Producing Parametric Maps Using Subband Acoustic Compensation" filed Nov. 25, 2013;

U.S. Pat. No. 9,724,072, titled "System And Method For Mixed Modality Acoustic Sampling" filed Dec. 13, 2013;

U.S. Pat. No. 9,456,805, titled "System And Method For Acquiring Optoacoustic Data And Producing Parametric Maps Using Interframe Persistent Artifact Removal" filed Dec. 19, 2013;

U.S. Publication 2016/0199037, titled "System And Method For Acquiring Optoacoustic Data And Producing Parametric Maps thereof" filed Mar. 22, 2016;

U.S. Publication 2017/0035388, titled "System And Method For Mixed Modality Acoustic Sampling" filed Oct. 18, 2016;

U.S. Pat. No. 9,792,686, titled "System And Method For Acquiring Optoacoustic Data And Producing Parametric Maps Using Subband Acoustic Compensation" filed Nov. 17, 2016;

U.S. Publication 2017/0296151, titled "System And Method For Mixed Modality Acoustic Sampling" filed Jun. 30, 2017;

U.S. Publication 2013/0109950, titled "Handheld Optoacoustic Probe" filed Nov. 2, 2011;

U.S. Publication 2016/0296121, titled "Handheld Optoacoustic Probe" filed May 2, 2016;

U.S. Pat. No. 8,686,335, titled "System And Method For Adjusting The Light Output Of An Optoacoustic Imaging System" filed Dec. 31, 2011;

U.S. Pat. No. 9,528,936, titled "System And Method For Adjusting The Light Output Of An Optoacoustic Imaging System" filed Mar. 31, 2014;

U.S. Publication 2017/0108429, titled "System And Method For Adjusting The Light Output Of An Optoacoustic Imaging System" filed Dec. 27, 2016;

U.S. Pat. No. 9,330,452, titled "Statistical Mapping In An Optoacoustic Imaging System" filed Mar. 11, 2013;

U.S. Pat. No. 9,836,838, titled "Statistical Mapping In An Optoacoustic Imaging System" filed May 3, 2016;

U.S. Publication 2018/0061050, titled "Statistical Mapping In An Optoacoustic Imaging System" filed Nov. 6, 2017;

U.S. Pat. No. 9,610,043, titled "System And Method For Producing Parametric Maps Of Optoacoustic Data" filed Jun. 13, 2012;

U.S. Publication 2017/0100040, titled "System And Method For Producing Parametric Maps Of Optoacoustic Data" filed Dec. 21, 2016;

U.S. Publication 2013/0338501, titled "System And Method For Storing Data Associated With The Operation Of A Dual Modality Optoacoustic/Ultrasound System" filed Jun. 13, 2012;

U.S. Publication 2013/0338475, titled "Optoacoustic Imaging System With Fiber Optic Cable" filed Jun. 13, 2012;

U.S. Publication 2014/0194723, titled "Multi-Layer Coating For Optoacoustic Probe" filed Jan. 13, 2014;

U.S. Publication 2017/0150890, titled "Optoacoustic Probe With Multi-Layer Coating" filed Jan. 31, 2017;

U.S. Pat. No. 9,615,750, titled "Methods And Compositions For Carrier Agents And Clearing Agents Used In Optoacoustic Imaging Systems" filed Jun. 14, 2012;

U.S. Publication 2013/0116538, titled "Optoacoustic Imaging Systems And Methods With Enhanced Safety" filed Oct. 19, 2012;

U.S. Publication 2015/0297090, titled "Optoacoustic Imaging Systems And Methods With Enhanced Safety" filed Jan. 23, 2015;

U.S. Publication 2013/0289381, titled "Dual Modality Imaging System For Coregistered Functional And Anatomical Mapping" filed Nov. 2, 2012;

U.S. Pat. No. 9,757,092, titled "Method For Dual Modality Optoacoustic Imaging" filed Nov. 2, 2012;

U.S. Publication 2014/0039293, titled "Optoacoustic Imaging System Having Handheld Probe Utilizing Optically Reflective Material" filed Jan. 22, 2013;

U.S. Publication 2017/0014101, titled "Dual Modality Imaging System For Coregistered Functional And Anatomical Mapping" filed Sep. 27, 2016;

U.S. Publication 2013/0303875, titled "System And Method For Dynamically Varying The Angle Of Light Transmission In An Optoacoustic Imaging System" filed Nov. 2, 2012;

U.S. Pat. No. 9,445,785, titled "System And Method For Normalizing Range In An Optoacoustic Imaging System" filed Dec. 21, 2012;

U.S. Pat. No. 9,282,899, titled "System And Method For Detecting Anomalous Channel In An Optoacoustic Imaging System" filed Dec. 21, 2012;

U.S. Publication 2014/0005544, titled "System And Method For Providing Selective Channel Sensitivity In An Optoacoustic Imaging System" filed Dec. 21, 2012;

U.S. Publication 2016/0317034, titled "System And Method For Providing Selective Channel Sensitivity In An Optoacoustic Imaging System" filed Jul. 11, 2016;

U.S. Pat. No. 9,445,786, titled "Interframe Energy Normalization In An Optoacoustic Imaging System" filed Jan. 22, 2013;

U.S. Publication 2017/0000354, titled "Interframe Energy Normalization In An Optoacoustic Imaging System" filed Sep. 19, 2016;

U.S. Publication 2014/0206978, titled "Probe With Optoacoustic Isolator" filed Jan. 22, 2013;

U.S. Pat. No. 9,743,839, titled "Playback Mode In An Optoacoustic Imaging System" filed Mar. 15, 2013;

U.S. Publication 2017/0332916, titled "Playback Mode In An Optoacoustic Imaging System" filed Jul. 27, 2017;

7

U.S. Pat. No. 9,398,893, titled "System And Method For Diagnostic Vector Classification Support" filed Mar. 11, 2014;

U.S. Pat. No. 10,026,170, titled "System And Method For Diagnostic Vector Classification Support" filed Jul. 19, 2016

U.S. application Ser. No. 16/022,138, titled "System And Method For Diagnostic Vector Classification Support" filed Jun. 28, 2018;

U.S. Pat. No. 9,730,587, titled "Diagnostic Simulator" filed Mar. 15, 2013;

U.S. Publication 2017/0332915, titled "Diagnostic Simulator" filed Jul. 27, 2017;

U.S. Pat. No. 8,823,928, titled "Light Output Calibration In An Optoacoustic System" filed Mar. 15, 2013;

U.S. Pat. No. 9,163,980, titled "Light Output Calibration In An Optoacoustic System" filed Jul. 11, 2014;

U.S. Pat. No. 9,814,394, titled "Noise Suppression In An Optoacoustic System" filed Mar. 15, 2013;

U.S. Publication 2018/0078144, titled "Noise Suppression In An Optoacoustic System" filed Nov. 13, 2017;

U.S. Pat. No. 9,733,119, titled "Optoacoustic Component Utilization Tracking" filed Mar. 15, 2013;

U.S. Publication 2017/0322071, titled "Optoacoustic Component Utilization Tracking" filed Jul. 27, 2017;

U.S. Publication 2015/0101411, titled "Systems And Methods For Component Separation In Medical Imaging" filed Oct. 13, 2014;

U.S. Publication 2015/0305628, titled "Probe Adapted To Control Blood Flow Through Vessels During Imaging And Method Of Use Of Same" filed Feb. 27, 2015

U.S. Publication 2016/0187481, titled "Opto-Acoustic Imaging System With Detection Of Relative Orientation Of Light Source And Acoustic Receiver Using Acoustic Waves" filed Oct. 30, 2015;

Siegel R L, Miller K D, Jemal A. Cancer statistics, 2018. CA Cancer J Clin 2018; 67:7-30. doi:10.3322/caac.21387

Polyak K. "Heterogeneity in breast cancer". J Clin Invest 2011; 121:3786-3788. doi:10.1172/JCI60534

Perou C M, Sorlie T, Eisen M B, van de Rijn M, Jeffrey S S, Rees C A, et al. "Molecular portraits of human breast tumours". Nature 2000; 406:747-52. doi: 10.1038/35021093

Sorlie T, Perou C M, Tibshirani R, Aas T, Geisler S, Johnsen H, et al. "Gene expression patterns of breast carcinomas distinguish tumor sub-classes with clinical implications". Proc Natl Acad Sci USA. 2001; 98:10869-74. doi: 10.1073/pnas.191367098

Russnes H G, Lingjorde O C, Brresen-Dale A L, Caldas C. "Breast Cancer Molecular Stratification: From Intrinsic Subtypes to Integrative Clusters". Am J Pathol. 2017; 187:2152-2162. doi: 10.1016/j.ajpath.2017.04.022.

Kim Y J, Kim J S, Kim I A. "Molecular subtype predicts incidence and prognosis of brain metastasis from breast cancer in SEER database". J Cancer Res Clin Oncol. 2018; 144:1803-1816. doi: 10.1007/s00432-018-2697-2.

Clarke M. "Meta-analyses of adjuvant therapies for women with early breast cancer: the Early Breast Cancer Trialists' Collaborative Group overview". Ann Oncol. 2006; 10:59-62. doi:10.1093/annonc/md1238.

"Early Breast Cancer Trialists' Collaborative Group (EBCTCG). Effects of chemotherapy and hormonal therapy for early breast cancer on recurrence and 15-year survival: an overview of the randomised trials". Lancet. 2005; 365:1687-717. Doi: 10.1016/S0140-6736(05)66544-0.

Loibl S, GianniL. "HER2-positive breast cancer". Lancet. 2017 17; 389:2415-2429. doi: 10.1016/S0140-6736(16)32417-5.

Pinker K, Chin J, Melsaether A N, Morris E A, Moy L. "Precision Medicine and Radiogenomics in Breast Cancer: New Approaches toward Diagnosis and Treatment". Radiology. 2018; 287:732-747. doi:10.1148/radiol.2018172171.

Chen J, Wang Z, Lv Q, Du Z, Tan Q, Zhang D, et al. "Comparison of Core Needle Biopsy and Excision Specimens for the Accurate Evaluation of Breast Cancer Molecular Markers: a Report of 1003 Cases". Pathol Oncol Res. 2017; 23:769-775. doi: 10.1007/s12253-017-0187-5.

Valluru K S, Wilson K E, Willmann J K. "Photoacoustic Imaging in Oncology: Translational Preclinical and Early Clinical Experience". Radiology 2016; 280:332-349. doi: 10.1148/radiol.16151414.

Schellenberg M W, Hunt H K. "Hand-held optoacoustic imaging: A review. Photoacoustics". 2018 6; 11:14-27. doi: 10.1016/j.pacs.2018.07.001.

Neuschler E I, Butler R, Young C A, Barke L D, Bertrand M L, Böhm-Vélez M, et al. "A Pivotal Study of Optoacoustic Imaging to Diagnose Benign and Malignant Breast Masses: A New Evaluation Tool for Radiologists". Radiology. 2018; 287:398-412. doi: 10.1148/radiol.2017172228.

Neuschler E I, Lavin P T, Tucker F L, Barke L D, Bertrand M L, Böhm-Vélez M, et al. Downgrading and Upgrading Gray-Scale Ultrasound B I-RADS "Categories of Benign and Malignant Masses With Optoacoustics: A Pilot Study". Am J Roentgenol. 2018; 211:689-700. doi: 10.2214/AJR.17.18436.

Menezes G L G, Pijnappel R M, Meeuwis C, Bisschops R, Veltman J, Lavin P T, van de Vijver M J, Mann R M. "Downgrading of Breast Masses Suspicious for Cancer by Using Optoacoustic Breast Imaging". Radiology. 2018; 288:355-365. doi: 10.1148/radiol.2018170500.

Lundgren K, Holm C, Landberg G. "Cell Mol Life Sci. Hypoxia and breast cancer: prognostic and therapeutic implications". 2007; 64:3233-3247. doi: 10.1007/s00018-007-7390-6

Vleugel M. M., Greijer A. E., Shvarts A., et al: "Differential prognostic impact of hypoxia induced and diffuse HIF-1alpha expression in invasive breast cancer". J Clin Pathol 2005; 58: 172-177. DOI: 10.1136/jcp.2004.019885 van der Groep P, Bouter A, Menko F H, van der Wall E, van Diest P J. "High frequency of HIF-1alpha overexpression in BRCA1 related breast cancer Breast Cancer Res Treat". 2008; 111:475-80. doi: 10.1007/s10549-007-9817-z Gilkes D M, Semenza G L. "Role of hypoxia-inducible factors in breast cancer metastasis". Future Oncol. 2013; 9:1623-1636. doi: 10.2217/fon.13.92.

Kraby M R, Krüger K, Opdahl S, Vatten L J, Akslen L A, Bofin A M. "Microvascular proliferation in luminal A and basal-like breast cancer subtypes". J Clin Pathol. 2015; 68:891-897. doi: 10.1136/jclinpath-2015-203037.

Lin N U, Vanderplas A, Hughes M E, Theriault R L, Edge S B, Wong Y N, et al. Cancer 2012; 118:5463-5472. doi: 10.1002/cncr.27581.

Ugras S, Stempel M, Patil S, Morrow M. "Estrogen receptor, progesterone receptor, and HER2 status predict lymphovascular invasion and lymph node involvement". Ann Surg Oncol. 2014; 21:3780-3786. doi: 10.1245/s10434-014-3851-y.

Yang W T, Dryden M, Broglio K, Gilcrease M, Dawood S, Dempsey P J, et al. "Mammographic features of triple receptor-negative primary breast cancers in young pre-menopausal women". Breast Cancer Res Treat. 2008; 111:405-410. doi: 10.1007/s10549-007-9810-6

Wang Y, Ikeda D M, Narasimhan B, et al. "Estrogen receptor-negative invasive breast cancer: imaging features of tumors with and without human epidermal growth factor receptor type 2 overexpression". Radiology 2008; 246:367-375. doi: 10.1148/radiol.2462070169

Uematsu T, Kasami M, Yuen S. "Triple-negative breast cancer: correlation between M R imaging and pathologic findings". Radiology 2009; 250:638-647.

Dogan B E, Gonzalez-Angulo A M, Gilcrease M, Dryden M J, Yang W T. "Multimodality imaging of triple receptor-negative tumors with mammography, ultrasound, and MRI". AJR Am J Roentgenol. 2010; 194:1160-1166. doi:10.2214/AJR.09.2355.

Wang C, Wei W, Santiago L, Whitman G, Dogan B. "Can imaging kinetic parameters of dynamic contrast-enhanced magnetic resonance imaging be valuable in predicting clinicopathological prognostic factors of invasive breast cancer?" Acta Radiol. 2018; 59:813-821. doi: 10.1177/0284185117740746.

Huuse E M, Moestue S A, Lindholm E M, Bathen T F, Nalwoga H, Krüger K et al. "In vivo MRI and histopathological assessment of tumor microenvironment in luminal-like and basal-like breast cancer xenografts". J Magn Reson Imaging. 2012; 35:1098-1107. doi: 10.1002/jmri.23507.

Ye I C, Fertig E J, DiGiacomo J W, Considine M, Godet I, Gilkes D M. "Molecular Portrait of Hypoxia in Breast Cancer: A Prognostic Signature and Novel HIF-regulated Genes". Mol Cancer Res. 2018 Jul. 23. pii: molca-nres.0345.2018 doi: 10.1158/1541-7786.MCR-18-0345.

Viale G, Giobbie-Hurder A, Regan M M, Coates A S, Mastropasqua M G, Dell'Orto P, et al. "Breast International Group Trial 1-98: Prognostic and predictive value of centrally reviewed Ki67 labeling index in postmenopausal women with endocrine-responsive breast cancer: results from Breast International Group Trial 1-98 comparing adjuvant tamoxifen with letrozole" J Clin Oncol 2008; 26:5569-5575. doi: 10.1200/JCO.2008.17.0829.

Parker J S, Mullins M, Cheang M C, et al. "Supervised risk predictor of breast cancer based on intrinsic subtypes". J Clin Oncol. 2009; 27:1160-1167. doi: 10.1200/JCO.2008.18.1370.

Prat A, Pineda E, Adamo B, et al. "Clinical implications of the intrinsic molecular subtypes of breast cancer". Breast. 2015; 24 Suppl 2:S26-35. doi: 10.1016/j.breast.2015.07.008.

Definitions

The term "labeled data set" refers to a combination of i) OA feature scores for OA images from an examination a patient, and ii) a class designation or outcome designator that has been determined for lesions and recorded with the OA feature scores. A labeled data set for an individual may include the set of medical diagnostic images from which the OA feature scores were obtained. The labeled data set may include non-OA feature scores for non-OA images from an examination of the patient. As another example, the labeled data set may include OA/non-OA feature scores that are created from combining information from the OA images and non-OA images. A labeled data set may correspond to an individual patient and/or a group of multiple patients for which corresponding multiple examinations have been obtained. The class designation in the labeled data set indicated that a lesion is benign or malignant.

The terms "optoacoustic image" and "OA image" refer to an image captured by an optoacoustic imaging system that utilizes transmit light at one or more frequencies into a volume of interest and receives an ultrasound data set that is processed and converted into an OA image.

The term "non-OA image" refers to any medical diagnostic image, other than an OA image, captured by one or more medical imaging modalities. A non-OA image constitutes an image that is captured based on an imaging principle that does not utilize transmission of optical light in two distinct frequency ranges to cause a volume of interest to generate acoustic signals. Non-limiting examples of non-OA images include ultrasound (US) images (transmissive and/or reflective), MRI images, X-ray images, CT images, PET images, and SPECT images. When the non-OA image is a US image, the US image may be captured by a US imaging system that is integrated with, coupled to or entirely separate from, an OA imaging system.

The terms "feature" and "feature of interest" refer to features of an OA image, US image and feature combinations thereof. The non-OA features may be US features, MRI features, X-ray features, CT features, PET features, SPECT features or another medical diagnostic imaging modality. Nonlimiting examples of OA features include 1) internal vascularity and de-oxygenation, 2) peri-tumoral boundary zone vascularity and deoxygenation, 3) internal deoxygenated blush, 4) internal total blood, 5) external peri-tumoral radiating vessels, and 6) interfering artifact. Non-limiting examples of ultrasound features include 1) US Shape Score, 2) US Internal Texture, 3) US Sound Transmission, 4) US Capsular or Boundary Zone, 5) US Peripheral Zone, 6) Patient Age, 7) Mammogram-BIRADS, 8) Lesion Size (cm), and 9) Lesion Posterior Depth (cm). Additional and alternative features are described in U.S. Pat. No. 9,398,893, to Anthony Thomas Stavros et al., titled "system and method for diagnostic vector classification support", filed Mar. 11, 2014 as application Ser. No. 14/205,005, and issuing Jul. 26, 2016 (hereafter the Stavros '893 patent), the complete and total subject matter of which is expressly incorporated herein by reference in its entirety.

The term "feature score" refers to a grade, rating, ranking or other evaluation information that is descriptive of one or more characteristics of a feature in an OA image and/or non-OA image. Non-limiting examples of feature scores include i) a numeric value along a range of numeric values, ii) a dimension measured from an OA or non-OA image, and/or iii) a word, phrase, or sentence describing a characteristic of the feature.

The term "observation" refers to one or more OA images (alone or in combination with one or more non-OA images) that are collected from a patient during an OA examination. The observation may also include diagnostic information entered by a clinician, such as OA feature scores and/or non-OA feature scores.

Predictive Machine Learning Classifier

In accordance with embodiments herein, a predictive machine learning (PML) classifier builds and utilizes classification models in conjunction with optoacoustic imaging to assist radiologist in predicting whether lesions belong to a malignancy class or a benign class. The PML classifier builds models that assign probabilities to the predictions. One unique aspect herein is the manner in which the PLM classifier builds the models to assign the probabilities to the predictions based on certain types of thresholds. In order to provide predictions, the PML classifier combines probability with one or more thresholds. The criteria for where to set the thresholds are separate from building the models. In embodiments herein, the criteria are set based on training labeled data that is collected from numerous individuals and analyzed by readers. The criteria are further set based on the premise that, if certain thresholds were applied to the study data, a predictive result would yield a desired level of sensitivity (e.g., 98%). In contrast, conventional approaches may set a threshold based on business factors, cost, greater penalty for false positive or false negative. In accordance with aspects herein, data from one or more studies were utilized to train the models to achieve the desired level of sensitivity.

Embodiments herein provide a PML classifier and classification models which is a software tool used in conjunction with an optoacoustic (OA) imaging system to assist radiologists in determining whether a breast lesion has a high enough risk of cancer to warrant a biopsy. The input to the classification models includes a set of feature values (e.g., OA and US Feature scores) that are assigned by the radiologist or sonographer and an output that includes an estimated likelihood of malignancy (LOM). The following description provides an overview of the underlying concepts of the machine learning classifiers, training methods, and performance metrics. The description explains fundamentals of the PML classifier and classification models that will remain constant as specific models evolve over time. The PML classifier and classification models is configured to be used by radiologists as an aid in the assessment of OA and ultrasound (US) images. Predictions made by the PML classifier and classification models are limited by the inherent statistical nature of classification algorithms and more importantly by the data used to train the classification models. In certain embodiments, predictions by the PML classifier and classification models may take into account a select portion of the information that is available to the radiologist. Yet in certain embodiments, the PML classifier and classification models can act as a second opinion to suggest when a radiologist should re-examine the image and reconsider an assessment.

Basic Model

At a base level, models may be constructed that include a Prediction for Classification (NPC) model and a Prediction for POM (NPP) model, where POM represents a Probability of Malignancy. The NPC and NPP models utilize various US and OA feature scores and can be trained based on a set of feature scores assigned by a human expert while viewing lesions that are present in a data set of images collected from a group of individuals.

While the NPC and NPP models are beneficial, there is an important distinction between an NPP model and an NPC model. The NPC model represents a logistic regression classifier that is trained based on biopsy outcomes (e.g., malignant or benign). Conversely, the NPP model represents a linear regression equation that is trained based on POM estimates that are assigned by the human expert. Whereas the NPC model predicts the biopsy results, the NPP model predicts the reader's estimate of the POM. The biopsy result is a binary outcome: malignant or benign. The POM is a continuous value between 0.0 and 1.0, inclusive. Biopsy results cannot be used for training the NPP model because the dependent variable in a linear regression equation must be a continuous value and not a binary category.

The base models may be applied as a heuristic rule, wherein a human expert is instructed to only downgrade a lesion's OA breast imaging reporting and data system (BI-RADS) category from the original US BI-RADS category if the average of NPP and NPC probabilities is at or below a probability threshold (e.g., 10% or less). Although this heuristic guards against excessive downgrading of malignant lesions, the probability threshold may not be accurate enough to be used directly for predicting a likelihood of malignancy.

In accordance with embodiments herein, predictive machine learning (PML) classification models have been developed that provide a better predictor of the likelihood of malignancy, as compared to the base models discussed above. As the name implies, the PML classification models are trained using predictive machine learning methods and a supporting software framework.

FIG. 1 illustrates a block diagram of the basic components of a PML classification system in accordance with embodiments herein. The PML classification system 100 includes one or more computing devices 120 that represent "reader computers" utilized by clinicians to analyze an individual patient's data set of OA/US images and other medical information related to the individual patient. The computing device 120 may be implemented as various types of computers, such as a workstation, a laptop computer, a tablet device, a smart phone and the like. The computing device 120 includes one or more processors executing program instructions stored in memory to provide, among other things, a graphical user interface (GUI) 104. The GUI 104 enables radiologists and other experts to enter features scores and view the predictive results. The GUI 104 may be developed in any suitable web language, such as HTML and JavaScript. The GUI 104 may be tailored for different situations, such as feasibility studies, pivotal studies, and commercial use. The GUI 104 may be implemented on any appropriate platform, including tablets and workstations. The GUI 104 is independent of the classification models 102.

The computing device 120 further includes an application programming interface (API) 108. The API 108 presents a protocol that defines the communication between the GUI 104 and the remote computing server 106. The API 108 is a set of rules for communication between the classification models 102, GUI 104 and server 106. The API 108 decouples the GUI 104 from the computation software implemented by the server 106 which simplifies the development and verification of the PML classifier and classification models, and encourages the building of GUIs 104 for various platforms such as tablets, smart phones and workstations.

The computing devices 120 communicate with a remote computing server 106. Nonlimiting examples of entities that may implement the remote computing server 106 include a medical network, a medical facility, a manufacturer of imaging equipment, a third-party data management service, third-party diagnostic image screening services, and the like. The computing server 106 includes one or more processors executing program instructions, to implement the operations described herein, as well as other operations associated with medical diagnostic imaging, diagnosis, therapy planning, therapy delivery and the like. The server 106 receives requests from the API 108, computes predictions, and returns the predictive results. The program instructions for the server 106 may be installed on computers in remote data centers, on a local network, one or more workstations, laptop computers, handheld electronic devices (e.g., tablet device, smart phone), the same physical device as the GUI 104 and the like.

The remote computing server 106 includes one or more processors implementing program instructions to provide a web service manager, a network service interface 134, and a PML classifier 136. The web service manager 132 receives request from computing devices 120 and returns corresponding replies. The network service interface 134 provides an interface between the web service manager 132 and the PML classifier 136. The remote computing server 106 includes a data storage 138 that comprises, among other things, classification models 102. As explained herein, the classification models may be organized in various manners, such as one or more ensembles of classification models 102. In accordance with certain types of PML classifiers 136, each classification model 102 may be built to include one or more decision trees (e.g. 10, 50, 100 decision trees in one classification model).

The classification models 102 are defined by a mathematical algorithm, independent variables representing features, and parameters determined by training based on one or more labeled data sets for a control group of individuals. The infrastructure of the PML classification system 100 allows for multiple models 102 to be built in order to better support various feature sets and improvements over time. For example, one ensemble of classification models 102 may be utilized with OA features only, while another ensemble of classification models 102 may be utilized with a combination of OA and US features. As a further example, one ensemble of classification models 102 may be utilized in connection with a first subtype of malignancies, while another ensemble of classification models may be utilized in connection with a second subtype of malignancies.

The classification models 102 may be developed and trained by a PML classifier 136 that utilizes various languages, such as the R language for statistical computing and graphics. For example, the server 106 implements the PML classifier 136 as a set of R scripts that compute classification probabilities from the classification models 102. The classification models 102 are not a single model; but rather a collection or ensemble of models that utilize different algorithms, features, and training data sets. The classification models 102 implement classification through machine learning in which the models are trained based on labeled data for OA images and non-OA images. For example, the classification models 102 may be built with a master model that is built based on all or substantially all of the available labeled data set, and may be built to include one or more bootstrapped models and hold out models. Bootstrapped models represent classification models that are formed from a select subset of the labeled data set. Hold out models represent classification models that are formed utilizing cross validation or another related model evaluation technique. In embodiments herein, the classification is a pattern recognition problem that uses a binary classifiers, as a special case in which there are only two outcomes. The classifier may have many classes. For example, a set of animal images can be classified as "cat", "dog", "bird", etc. In mathematical terms, the class label is a categorical variable. When the classifier is applied to an observation, it estimates the probability that the observation belongs to a particular class. The PML classifier and classification models does not decide the class; instead the PML classifier and classification models apply a threshold (or cut point) that results in a prediction. The choice of the threshold may vary.

Each classification model 102 is defined by three elements: an algorithm, features, and parameters, which are described hereafter in general, along with an explanation for a model "learns" from a training data set. Classification approaches are of two basic types: parametric equations and machine learning algorithms. Parametric equations are more transparent in that the effect of each feature is easy to understand. However equations are limited in what they can model. Machine learning methods can be applied more broadly, but it is often difficult to understand how the model works and what it finds important.

Embodiments herein utilize machine learning algorithms within the PML classifier 136. Non-limiting examples of machine learning algorithms include classification and regression trees (CART), C4.5 decision trees, K nearest-neighbor, Support Vector Machines (SVM), and Naïve Bayes classifiers. Irrespective of the algorithm, a single model often suffers from either inaccuracy or overfitting. To overcome the potential for inaccuracy or overfitting, embodiments herein train and utilize multiple models to generate multiple predictions for an observation. The collection of the classification models are referred to as an "ensemble" of models. Embodiments herein utilize the random forest algorithm to form an ensemble of decision trees and/or the extreme gradient boosting (XGB) algorithm to form an ensemble that can be used with CART decision trees or with linear classifiers. The XGBOOST algorithm often outperforms other algorithms when properly tuned and can be used on massive data sets.

Figure 2A:
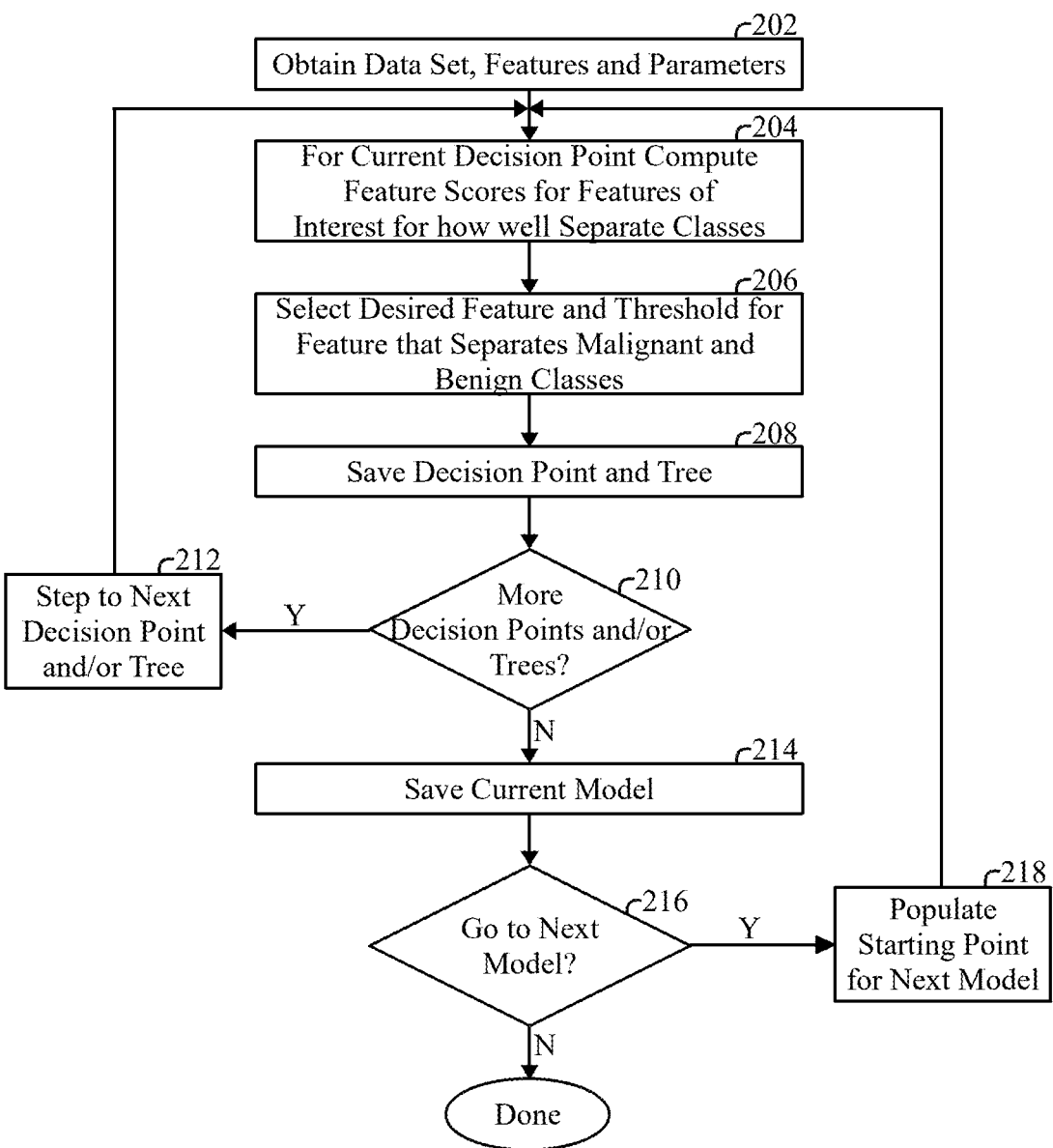
FIG. 2A illustrates a process for building an ensemble of classification models in accordance with embodiments herein.

FIG. 2A illustrates a process for building an ensemble of classification models in accordance with embodiments herein. The operations of FIG. 2A may be implemented by processors at a system located at one location, or server or distributed between multiple remote locations or servers.

At 202, the one or more processors obtain a labeled data set for multiple patients, along with a collection of features and parameters. The operations at 204-218 step through the labeled data set in various manners, based on the type of PML classifier algorithm being utilized to build the ensemble of classification models. It is recognized that the particular branches, decision points and order of operations described in connection with FIG. 2A will vary within embodiments contemplated herein, but still result in an ensemble of classification models as described herein.

At 204, the one or more processors begin analyzing the labeled data set for a current decision point in a current decision tree. The processors compute outcome scores for one or more features of interest. The outcome scores are indicative of how well a particular feature of interest separates the labeled patient data into the malignant class or the benign class.

At 206, the one or more processors review the outcome scores and select the desired feature, as well as a threshold to be applied to the feature. The feature and threshold selected at 206 may represent the "best" feature and threshold that separate the labeled data set into malignant and benign classes based on the present point in the decision tree.

Example features are described in the Stavros '893 patent. The features represent a set of independent variables, for which values may be of any type (continuous, interval, ordinal, or categorical). Feature definition generally impacts success of a model. Moreover, better features simplify the model and make it easier to interpret results. Feature engineering is the process of creating, testing, and improving features. Feature selection is a trade-off between including all relevant features and avoiding extra features that can lead to over-fitting. Excess features also adversely affect training because the amount of data required generally grows exponentially with the number of features.

Parameters define the various classification models utilized herein. As a non-limiting example, the parameters in machine learning based models define branching criteria in a decision tree. To further illustrate the parameters, consider a decision tree for predicting if a lesion is malignant based on lesion shape, orientation, and margin. The first branch, or decision point, uses the feature that provides the most information in separating malignant from benign lesions. Round shapes may take one branch and all other shapes another branch. At another decision point, orientations in one range may take one branch while orientations in another range may take another branch.

Although learning methods vary depending upon the algorithm, the core of the mathematics is an iterative search over the feature space. Iterative searching is computationally intensive, especially when there are a large number of features and/or a large amount of data. Reducing the search space speeds up the process but tends to find a less optimal solution. As before, consider decision trees as an example. Decision trees learn by finding the optimal criteria to split the tree into branches. Each path through the tree ends up at a leaf and the goal is to find the splits, or decision points, such that each leaf contains mostly one class. The feature chosen for a split is found by considering all possible features and their values, and selecting the feature that provides a desired result (e.g., the best one). As one example, the selection may be whether to use a boundary score or an internal vessel score as the feature to analyze at the decision point. In addition to selecting the feature to use at each branch, the PML classifier also determines what threshold level to apply to the feature at the decision point. For example, when boundary score is selected as the feature of interest at a particular branch point, then the PML classifier also assigns a boundary threshold, such that when the boundary score is above the boundary threshold, the decision branches in a first direction and when the boundary score is below the boundary threshold, the decision branches in a second direction.

As one example, the operations at 204, 206 may be performed by computing a score called a "Gini impurity index" which is used to choose a split with the lowest score. Each split considers many features, a tree contains multiple splits, and an ensemble contains many trees. Beyond the feature level parameters, embodiments may utilize machine learning algorithms that have hyper-parameters that are tuned. For example, embodiments that use XGBOOSTtrees have a large set of hyper-parameters, including the number of trees, the maximum tree layer depth, and the learning rate. Hyper-parameters add dimensions to the search space and hence increase the computation effort for training.

At 208, the one or more processors save the decision point within a current decision tree. At 210, the one or more processors determine whether the analysis should continue for more decision points in the current decision tree and/or whether the analysis should continue for a next the decision tree. If so, flow branches to 212. Otherwise, flow continues to 214. At 212, the one or more processors step to the next decision point in the current decision tree. For example, branching continues until the maximum tree depth, a lesion trait is identified or other criteria are met. The number of branches, the features used at each branch, and values used for separation at each branch are all parameters of the model. In essence, the parameters embody the training data. Good parameters result from a combination of attention to detail in features, data, and algorithm tuning. When a decision tree is finalized, the processors also assign lesion traits (e.g. benign class, malignant class, cancer subtype) to the last layer. The lesion traits may be stored with a classification probability based on the individual corresponding decision tree.

Alternatively, when a decision tree is completed at 210 and a new decision tree is to be started, the operation at 212 steps to the next decision tree and flow returns to 204. The operations at 204-212 are continuously operated until all of the decision points in a desired number of decision trees are built.

At 214, the one or more processors save, as a current model, the collection of decision trees, each of which is comprised of a set of decision points built from the feature scores, feature selections and threshold selections described above.

At 216, the one or more processors determine whether another model is to be built from the labeled data set. If so, flow branches to 218. At 218, the one or more processors populate starting points within the next model. Otherwise, the process of FIG. 2A ends.

In accordance with the operations of FIG. 2A, and/or alternative sequences of operations, embodiments herein fit the model parameters to the labeled data set through a training or learning process. The training/learning process is also referred to as "building" the model.

Next, two examples of predictive machine learning algorithms are described that may be implemented in connection with embodiments herein.

Logistic Regression Models

One example of a predictive machine learning algorithm that may be implemented herein is logistic regression. Logistic regression is a supervised machine learning algorithm because it uses true labels for training. A supervised learning algorithm has input variables (x) and an target variable (Y) when the model is train, as in logistic regression algorithms. Embodiments herein form an ensemble of logistic regression models (e.g., 100), each trained on a subset of the control data set. The prediction is returned as the mean confidence interval (likelihood of malignancy or LOM) and a confidence interval range (e.g., 90%) of the predictions from the ensemble. The prediction is returned as the Positive Predictive Value (PPV) that corresponds to the classifier probability.

The logistic regression models utilize a training data set that comprises a collection of observations or reads (e.g., 100, 1000, 10000). Each of the observations contains a set of OA images, US images, combinations of OA/US images, OA feature scores, and US feature scores. The OA and US feature scores may be assigned automatically by a computing system that segments and analyzes the OA, US and combined images. Additionally or alternatively, the OA and US feature scores may be assigned by one or more human independent reader. The OA and US scores relate to one or more characteristics of one or more lesions in the OA and US image set for an individual patient. The training data set includes a collection of images for a number of positive cases (malignant) and a number of negative cases (benign).

The logistic regression model utilizes a feature set that includes reader-assigned scores for OA and US features, the patient age and the mammogram (MMG) BI-RADS category assigned by the site radiologist. The MMG BI-RADS is not defined for all observations. By way of example, the logistic regression model includes 5 or more OA feature scores, 5 or more US feature scores, age, and MMG BI-RADS applied in a heuristic rule. For example, the MMG BI-RADS heuristic rule may be defined as {2, 3, 4a, 4b, 4c, 5}. Initially, MMG BI-RADS may not be utilized as a feature in the logistic regression algorithm because too many lesions in the data set may be missing MMG data. However, once a data set collects a sufficient amount of MMG data the logistic regression algorithm can be trained on the subset of data with MMG data. Optionally, even while the MMG BI-RADS may not be utilizes as a feature, the MMG BI-RADS may be applied as a heuristic rule that prohibits a downgrade if the MMG BI-RADS is at a certain level (e.g., 4c or 5). For cases with a MMG BI-RADS rating at or above the set level, the SenoGram returns the maximum of the classifier prediction and the benchmark PPV for the category, computed as the midpoint of the range (e.g. 70% for 4c, and 95% for 5). The MMG BI-RADS heuristic rule is not applied if the MMG BI-RADS rating is missing or inconclusive.

The foregoing logistics regression machine learning algorithm was evaluated using repeated K-fold cross-validation with 5 repeats and 10 folds. Metrics were averaged over the 50 test sets to obtain the following approximate results: AUC between 0.92 and 0.96, pAUC between 0.75 and 0.80, sensitivity at or above 97.0%, specificity at or above 52.0%.

Extreme Gradient Boost Trees (XGBTree)

Additionally or alternatively the machine learning algorithm (PML classifier) may be implemented utilizing an Extreme Gradient Boosting Trees (XGBTree) machine learning algorithm. In order to understand the XGBTree, the decision tree should first be understood. Decision trees are a method of splitting the data based on features to either classify or predict some value. Each branch in a decision tree divides the data into one of two (or several, if the tree is not binary) groups. Each leaf node is allocated with a single label (class or predicted value). When predicting using the decision tree, the data is allocated to the appropriate leaf node, and the prediction is the label of that leaf node. Decision trees are flexible and interpretable. However, a single decision tree is prone to overfitting and is unlikely to generalize well. There are various ways of restricting the flexibility of a decision tree, such as by limiting its depth, but those methods then cause the decision tree to underfit. This is why decision trees are generally not used alone: instead, multiple decision trees are used together. Gradient boosting decision trees are one method (among many) of combining the predictions of multiple decision trees to make predictions that generalize well. Despite their strength, the idea behind XGBTree algorithms is very basic: combine the predictions of multiple decision trees by adding the predictions together. XGBTrees are trained iteratively—i.e. one tree at a time. For instance, the XGBTree algorithm first train a simple, weak decision tree based on the data. The decision tree is trained to minimize an objective function—using a lost term—such as the mean squared error—by recursively splitting the data in a way that maximizes some criterion until some limit-such as the depth of the tree—is met. The criterion is chosen so that the loss function is (approximately) minimized by each split. One commonly used criterion is the classification accuracy which is the fraction of observations that are correctly partitioned by the split.

The training of a decision tree is a recursive processing. The next tree is then trained to minimize the loss function when its outputs are added to the first tree. This is (approximately) achieved by recursively splitting the data according to a new criterion. For example, the criterion can be simply calculated for any split of data based on the gradient statistics (the value of the gradient for each data point). It should be noted that computing the best split requires the model to go through various splits and compute the criterion for each split. There is no analytical solution for determining the best split at each stage.

The XGBTree machine learning algorithm forms an ensemble of XGBTree models, each trained on all or a subset of a data set. As with the logistics regression machine learning algorithm, the prediction is returned as the mean and 90% confidence intervals of the ensemble, with the classification probability mapped to the observed PPV in the training data. The XGBTree machine learning algorithm may utilize the same or different training data as the logistic regression MLA. Additionally, the XGBTree MLA may also utilize individual human expert data. The XGBTree MLA utilizes the same features as for logistic regression MLA, with the possible addition of artifact scores, lesion size and/or lesion orientation. The MMG BI-RADS category may be included as a feature of the XGBTree MLA rather than applied in a heuristic rule, depending upon the amount of missing MMG data.

When growing the XGBTree, both XGBoost and lightGBM use the leaf-wise growth strategy. When training each individual decision tree and splitting the data, there are two strategies that can be employed: level-wise and leaf-wise. The level-wise strategy maintains a balanced tree, whereas the leaf-wise strategy splits the leaf that reduces the loss the most. Level-wise training can be seen as a form of regularized training since leaf-wise training can construct any tree that level-wise training can, whereas the opposite does not hold. Therefore, leaf-wise training is more prone to overfitting but is more flexible. This makes it a better choice for large datasets. Compared to the case of level-wise growth, a tree grown with leaf-wise growth will be deeper when the number of leaves is the same. This means that the same max_depth parameter can result in trees with vastly different levels of complexity depending on the growth strategy.

An important challenge in training the XGBTree is the process of finding the best split for each leaf. When naively done, this step requires the algorithm to go through every feature of every data point. The computational complexity is thus $O(n\_\{data\}n\_\{features\})$. Modem datasets tend to be both large in the number of samples and the number of features. For instance, a tf-idf matrix of a million documents with a vocabulary size of 1 million would have a trillion entries. Thus, a naive GBDT would take forever to train on such datasets. There is no method that can find the best split while avoiding going through all features of all data points. Therefore, the various methods that XGBoost and lightGBM present are methods of finding the approximate best split.

Optionally, histogram-based methods (XGBoost and lightGBM) may be utilized. The amount of time it takes to build a tree is proportional to the number of splits that have to be evaluated. Often, small changes in the split don't make much of a difference in the performance of the tree. Histogram-based methods take advantage of this fact by grouping features into a set of bins and perform splitting on the bins instead of the features. This is equivalent to subsampling the number of splits that the model evaluates. Since the features can be binned before building each tree, this method can greatly speed up training, reducing the computational complexity to $O(n\_\{data\}n\_\{bins\})$. Though conceptually simple, histogram-based methods present several choices that the user has to make. Firstly the number of bins creates a trade-off between speed and accuracy: the more bins there are, the more accurate the algorithm is, but the slower it is as well. Secondly, how to divide the features into discrete bins is a non-trivial problem: dividing the bins into equal intervals (the most simple method) can often result in an unbalanced allocation of data. XGBoost offers the option tree_method=approx, which computes a new set of bins at each split using the gradient statistics. LightGBM and XGBoost with the tree_method set to histogram will both compute the bins at the beginning of training and reuse the same bins throughout the entire training process.

The operations of FIG. 2A or another model building process may be implemented multiple times utilizing different combinations of the available labeled data set of the control patient population. For example, all or a majority of the label data set for all or majority of the patient population may be utilized to build a master model. In accordance with embodiments herein, the master classification model is then utilized to calculate predictive results and the like.

In addition, the labeled data set may be subdivided into folds or subsets, wherein different subsets of the observations in the labeled data set are defined as "hold out" observations. Hold out models are built during cross validation utilizing the portions of the label data set that was not held out. As explained herein, the held out portions of the labeled data set may then be applied to the hold out models in connection with calculating classification probabilities, from which mapping functions are built for positive predictive values, false-negative rates and the like.

Additionally or alternatively, subsets of the observations from the labeled data set may be utilized to build bootstrapped models. For example, the labeled data set may include 100 observations, from which a random sampling of the observations are selected and utilized to build a first bootstrapped model. Multiple bootstrapped models are built based on different combinations of samples of the observations from the labeled data set for the control patient population. Once the classification models are built, when new observations for new patients are obtained, the bootstrapped models are then utilized in connection with calculating predictive results, namely for calculating a prediction interval for the new OA and non-OA feature scores.

Figure 2B:
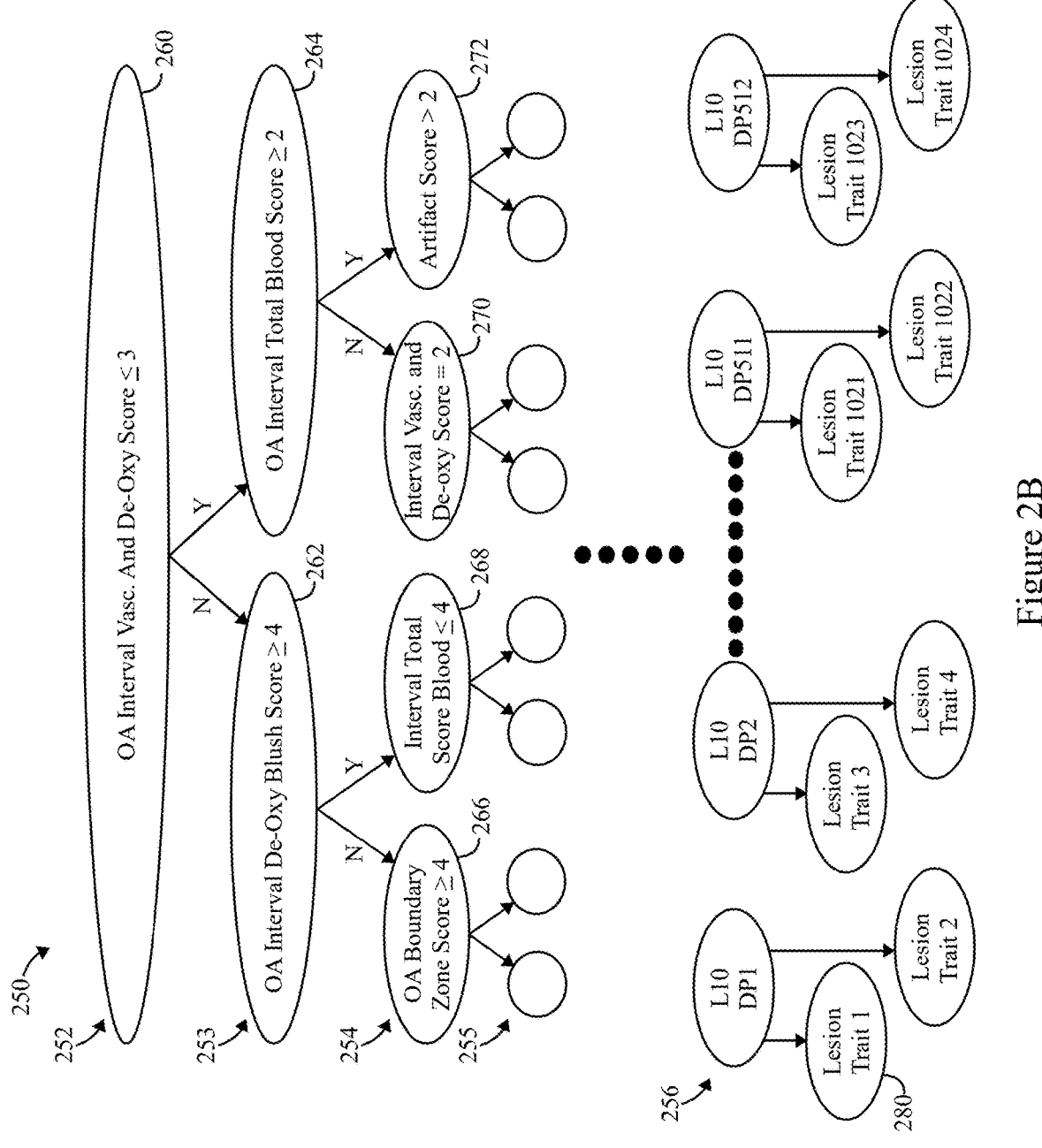
FIG. 2B illustrates an example of a decision tree from a classification model built in accordance with embodiments herein.

FIG. 2B illustrates an example of a decision tree from a classification model built in accordance with an embodiment herein. For example, the decision tree 250 may be built by the XGBtree algorithm during one or more iterations through the operations of FIG. 2A. Alternatively, the decision tree 250 may be built from an XGBtree or other algorithm following operations that differ from FIG. 2A. The decision tree comprises decision points, branches between decision points and lesion traits. Lesion traits are obtained from multiple decision trees and mathematically combined to form a classification probability that a lesion exhibits a particular trait for a corresponding observation (e.g. based on the OA and non-OA feature scores assigned to the OA and non-OA images of the examination). The decision tree 250 includes multiple layers 252-265, including first through tenth layers. The tenth layer 256 is also denoted by the labels "L10". Each layer 252-256 includes a set of decision points (DP). Each decision point tests a feature of interest relative to a threshold. For example, the decision points may test the OA and US features described herein, where each OA and/or US feature score is compared to a threshold.

In the example of FIG. 2B, non-limiting examples of decision points are shown. A first decision point 260 in the first layer 252 may test whether the OA feature "internal vascularity and de-oxygenation" was given an OA feature score of "less than 3." Recall that the OA features are scored manually by a human expert and/or automatically by a classification support system as described in the Stavros '893 patent (or other documents incorporated herein by reference). The decision tree branches from DP 260 to decision points 262 and 264 in the second layer 253. As an example, the decision point 262 tests whether the OA feature "internal de-oxygenation blush" was given an OA feature score of "greater than or equal to 4," while the decision point 264 tests whether the OA feature "internal total blood" was given an OA feature score of "greater than or equal to 2." As other examples, the decision points 266, 268, 270, 272 test whether the OA features "peri-tumoral boundary zone vascularity and deoxygenation" was given an OA feature score of "greater than or equal to 4," and the like. The decision tree 250 continues for multiple layers until reaching a depth limit (e.g., 10 layers) as noted at L10_DP1 to L10_DP512. Each decision point in the $10^{th}$ layer branches to two lesion traits (LT) 280 based on the features to be tested and the score thresholds at layer 10. In the example of FIG. 2B, 1024 lesion traits (LT1 to LT1024) are available in a decision tree having 10 layers where each decision point splits into two branches.

The lesion traits may correspond to different information, depending upon the nature of the decision tree. For example, the lesion traits may simply represent one of two binary choices regarding a trait of a lesion, namely malignant class or benign class. For example, lesion traits 1-10, 20, 32-40 and 100-140 may designate the lesion trait to correspond to the malignant class, while the remaining lesion traits designate the lesion to correspond to the benign class. Additionally or alternatively, each lesion trait may include a classification probability associated therewith. For example, an output of a decision tree may designate a 40% likelihood that a lesion trait is in the malignant class. Optionally, when the decision trees are built to designate cancer subtypes, the lesion traits may be representative of more than two binary choices, instead designating a lesion trait to be one of various cancer subtypes and/or benign. Additionally or alternatively, a decision tree may output a classification probability that a lesion type corresponds to a cancer subtype or benign class.

The classification probability provides a level of confidence that the observation (e.g. set of OA and non-OA feature scores for a current patient) is in a particular class, namely either a malignant class or a benign class.

The example of FIG. 2B illustrates a binary type decision tree. Additionally or alternatively, the decision trees may include more than 2 branches from each node, when a test at each decision point includes more than 2 outcomes. The examples of FIG. 2B at decision points show OA feature score tests. It is recognized that many of the decision points will include tests for US feature scores with respect to US feature score thresholds. Additionally or alternatively, the score thresholds may not be simple numeric values, but instead be qualitative descriptors (e.g., dark, light, large, small, opaque), dimensions (e.g., diameter, thickness, length, width) and the like.

The PML classifier algorithm builds a master model that comprises multiple decision trees similar to decision tree 250 based on at least partially different labeled data sets, at least partially different features and/or at least partially different parameters. The feature set and parameters are adjusted as part of a trade-off of a false negative rate vs. likelihood of malignancy. Although the false negative rate is related to the likelihood of malignancy, it is a fundamentally different quantity. The difference is important because there is a dichotomy in the use of FNR, or sensitivity, for reporting clinical study results, and the use of PPV, or likelihood of malignancy, in the BI-RADS lexicon familiar to radiologists. While PPV and likelihood of malignancy are sometimes used interchangeably, this is not strictly correct, as likelihood of malignancy refers to the entire population; whereas PPV is an estimate of likelihood based on a sample of the population. The distinction is analogous to the difference between the population mean and the sample mean.

FNR, sensitivity and specificity are at least two of the preferred metrics for diagnostic tests because they are intrinsic to the test and do not rely on prevalence of the disease or condition in the study population. Conversely, PPV does depend upon prevalence; a higher prevalence increases the PPV. When PPV is reported for a study, the prevalence should also be reported.

In basic terms, the FNR is relative to total number of negatives in the full population, whereas the PPV is relative to the number of positives and negatives in a category of the full population. A more precise definition is given in the equation below, which compare the PPV for BI-RADS 3 to the FNR using a threshold between BI-RADS 3 and 4A:

$$FNR = \left[100\% \; \left(N_{Cancer,ADS_2} + N_{Cancer,BIRADS_3}\right)\right]/[N_{Cancer,Total}] \text{ and}$$

$$PPV_{BIRADS_3} = \left[100\% \times N_{Cancer,BIRADS_3}\right]/\left[\left(N_{Cancer,BIRADS_3} + N_{Benign,BIRADS_3}\right)\right],$$

where $N_{Cancer,BIRADS \; 2 \; (or \; 3)}$=number of reads that scored a malignant lesion as BI-RADS 2 (or 3), $N_{Benign,BIRADS \; 3}$=number of reads that scored a benign lesion as BI-RADS 3, and $N_{Cancer,Total}$=total number of reads of malignant lesions.

It should be noted that FNR and sensitivity depend only upon malignant lesions, whereas PPV depends upon the malignant and benign lesions. The threshold is chosen such that it corresponds to a desired FNR (e.g., 2%), which is equivalent to a desired sensitivity (e.g., 98%). The threshold is based on FNR because sensitivity and specificity are the primary metrics for imaging studies, as well as being the FDA metrics of choice for diagnostic tests. However sensitivity and specificity are summary statistics for a data set, and may not be as helpful to a radiologist's application of SenoGram results for an individual lesion.

In accordance with embodiments herein a more useful metric is provided to radiologists, namely the likelihood of malignancy for the lesion. The likelihood of malignancy can be estimated from measured PPVs for the data set. The American College of Radiology (ACR) provides a benchmark PPV for each BI-RADS category (see Table 1). The ACR benchmark PPVs for BI-RADS categories are based on clinical study data reported in the literature. Radiologists are accustom to applying the BI-RADS lexicon when making biopsy recommendations. The SenoGram adapts outputs of the MLA accordingly, and displays a predicted likelihood of cancer as shown in the attached Figures.

TABLE 1

| Likelihood of Malignancy for BI-RADS Categories | |
| --- | --- |
| BI-RADS Category | Likelihood of Malignancy (BI-RADS Atlas, 5th Ed.) |
| 3 | >0% but ≤2% |
| 4A | >2% but ≤10% |
| 4B | >10% but ≤50% |
| 4C | >50% but <95% |
| 5 | ≥95% |

Classification model PPVs are computed in a manner that maps the PPVs in a more fine-grained than simply computing BI-RADS PPVs for an entire category. Instead, the PML classifier provides a PPV for each of a plurality of percentage intervals (e.g., every 1-5% interval) in the classification probability. The PPV vs. probability data are fit to a nonlinear function, and the PML classifier applies the function to convert a classifier output to a likelihood of malignancy estimate that is displayed in the GUI.

Figure 3:
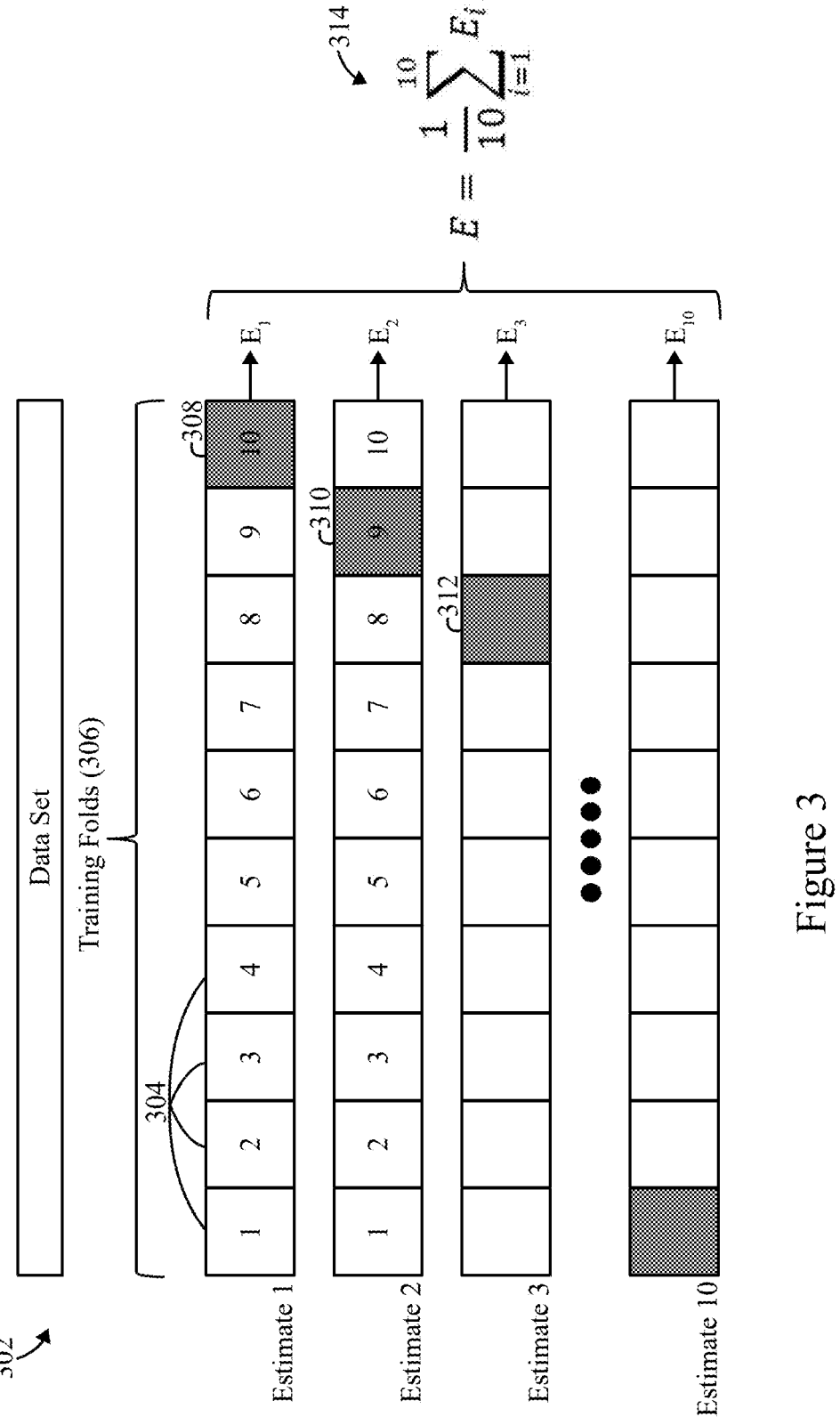
FIG. 3 illustrates an example of cross validation in accordance with an embodiment herein.
Figure 4:
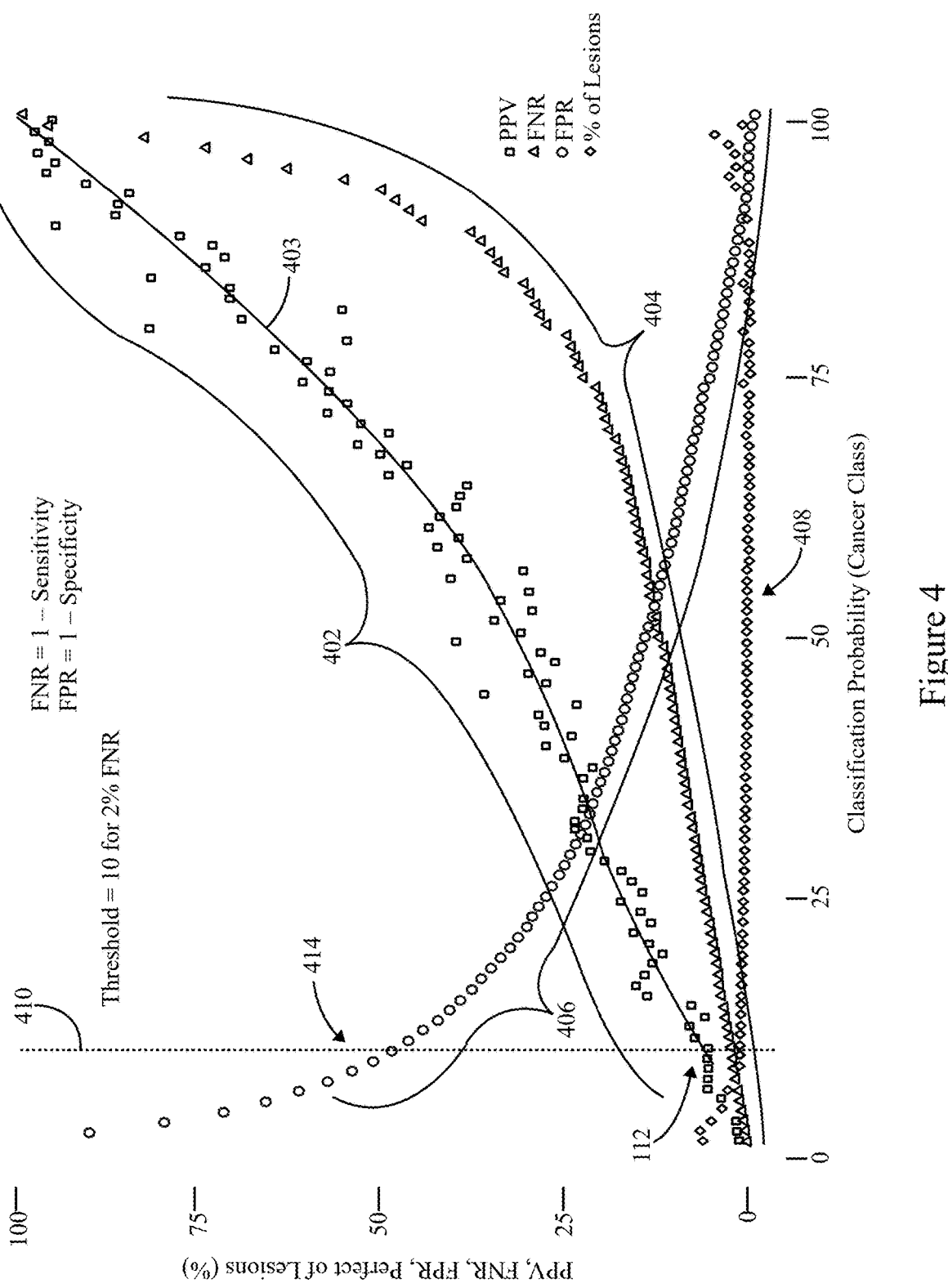
FIG. 4 shows the relationship between the classification probability and the measured PPV for embodiments herein.

FIG. 4 shows a group of mapping functions calculated in connection with a labeled data set for a control population in accordance with embodiments herein. In FIG. 4, the horizontal axis corresponds to classification probabilities that a lesion has been designated with a particular trait, such as in the malignant class. The horizontal axis is divided into bins corresponding to probability increments of a desired length, such as 1%. In accordance with embodiments herein, the processors of the server 106 build the mapping functions in FIG. 4 based on the classification probabilities calculated from the holdout models (described above in connection with FIG. 3). As noted herein, each holdout model is trained based on a portion of the label data set and thereafter a remaining portion of the label data set is applied to the corresponding holdout model to obtain classification probabilities. In the example of FIG. 3, 100 observations were utilized to generate 10 holdout models, each of which produced 10 classification probabilities, resulting in 100 classification probabilities.

The vertical axis of the graph in FIG. 4 corresponds to various statistical parameters that characterize the classification models and the labeled data set, including a positive predictive value (PPV), false negative rate (FNR), false positive rate (FPR) and percent of lesions. The processors of the server 106 sort the observations (in an ascending or descending order) from the label data set based on the classification probabilities generated by the holdout models. The processors then bin or group the observations, and corresponding classification probabilities, into the increments assigned to the horizontal axis of the graph in FIG. 4.

For example, consider the 1% probability increment between 79%-80%. The processors identify any observations having a classification probability between 79% and 80%. The classification probabilities are necessarily whole numbers and may have similar or the same classification probabilities. Thus, multiple observations may be binned into a single 1% probability increment. As a nonlimiting example, if the observations #5, #7, #10, #45, and #67 were applied to the corresponding holdout models, the observations #5, #7, #10, #45, and #67 could result in classification probabilities of 79.02, 79.07, 79.6, 79.8, and 79.92, respectively. Accordingly, the observations #5, #7, #10, #45, and #67 would be grouped into a single 1% probability increment within the graph of FIG. 4. The labeled data set for the observations #5, #7, #10, #45, and #67 are further analyzed to identify the actual diagnosis associated with the lesion, namely whether the lesion (after being biopsy) was determined to be malignant or benign. For example, after biopsies, the observations #5, #7, #10, and #45, may have been found to be malignant, while the observation #67 may have been found to be benign. A positive predictive value is calculated from the actual diagnoses as the number of observations that were malignant divided by the total number of observations (e.g., [4 malignant]/[5 total]) in the classification increment of 79% and 80%. A data point is then entered along the vertical axis at approximately 80% PPV and 79%-80% classification probability.

The foregoing process is repeated for each probability increment along the X axis until a PPV value is assigned to each probability increment. In the example of FIG. 4, the data points associating PPV to classification probability are noted by bracket 402. Based on the data points within bracket 402, the one or more processors calculate a mapping function 403 that maps classification probabilities to positive predictive values.

As explained herein in connection with FIG. 5A, the one or more processors of the server 106 may utilize PPV as a predictive result. To do so, the processors apply a new observation to the master classification model, to obtain a corresponding classification probability. The processors then utilize the classification probability for the new observation as an input into the mapping function 403. The mapping function 403 outputs a corresponding PPV value that is returned by the processors of the server 106 as the predictive result.

Additionally or alternatively, the processors of the server may calculate mapping functions associated with the FNR, FPR and the percent of lesions based on the labeled data set and the above-described binning of the classification probabilities. The PPV points are displayed in the area denoted by bracket 402, the FNR points are displayed in the area denoted by bracket 404, the FPR points are denoted by bracket 406, and the percent of lesions points are noted at 408.

FIG. 4 also illustrates a decision threshold 410 that is calculated by the processors of the server 106. The decision threshold 410 represents a point at which the clinician chooses whether to perform a biopsy or not perform a biopsy. To locate the decision threshold 410 within the graph of FIG. 4, the one or more processors first receive, as an input, a designation of a sensitivity or false negative rate (e.g., 2% FNR, or 98% sensitivity). The processors then applied the chosen FNR level along the Y axis until intersecting the mapping function for the FNR as designated by bracket 404 to identify the corresponding classification probability along the x-axis. In the example of FIG. 4, a 98% sensitivity or 2% FNR rate corresponds to a 10% classification probability. The 10% classification probability, when mapped to the PPR mapping function 403 corresponds to a PPR level of approximately 5%. Optionally, a biopsy/no biopsy threshold may be presented to the user corresponding to the PPR level associated with the decision threshold 410.

Model Evaluation

Once a model is trained, the model is tested before use. Embodiments herein separate the training process from the evaluation process. The final model uses the full data set for training, whereas evaluation of the model is done by dividing the data set into a training data set and a test data set. The training data set is used to build a provisional model and the test data set is used to evaluate the provisional model. The process is repeated with different splits of the data and the results are averaged to obtain an estimate of how the final model will perform.

A basic problem in learning is the trade-off between too much training ("over-fitting") and too little training ("weak learner"). Over-fitting makes a model brittle in that the models performs well on the training data but poorly on new data. Too little training produces in a robust model, but lowers the accuracy of the model. One solution herein to this dilemma is to use an ensemble that aggregates a collection of weak learners thereby producing an ensemble model that is both robust and more accurate. Building an ensemble model may increase training time, however parallel programming methods can reduce the training time to more reasonable levels. Expanding the amount and diversity of data in the training set improves the model, especially when there are a large number of features. For this reason, embodiments herein re-train models as more data becomes available. Re-training a model improves its accuracy and allows it to adjust as the population evolves.

In accordance with embodiments herein, once built, the master classification model and/or any other the classification models may be evaluated. Various algorithms exist for evaluating classification modules, such as K-fold cross-validation. During K fold cross validation, embodiments herein billed multiple "hold out" models as described hereafter.

FIG. 3 illustrates an example of a K fold cross validation process implemented in accordance with an embodiment herein. The K fold cross validation process builds holdout models that are evaluated to test the master classification model. In addition, the holdout models are utilized, as described herein, in connection with calculating mapping functions for classification probabilities to be utilized with subsequent patients. In cross validation the labeled data set 302 is randomly partitioned (e.g. with stratification) into folds 304. The processors (e.g. of the server 106) estimate performance for the master classification model by building and evaluating holdout models based on subsets of the folds 304.

For example, a first holdout model is trained utilizing the subset of training folds 306 (folds 1-9), while a "hold out" test fold 308 (fold 10) is not used to train the first model. Once the first holdout model is built, the observations from the holdout fold 308 are applied to the first holdout model to obtain corresponding classification probabilities. As a further example, it can be assumed that the labeled data set 302 includes 100 observations (corresponding to 100 different patient examinations for 100 different lesions). Each fold 304 would then include 10 observations. The first holdout model would be trained based on the 90 observations in the first nine folds, after which the final 10 observations from the holdout fold 308 would be applied to the first holdout model to obtain 10 corresponding classification probabilities (referred to as estimate 1 or E1). Each classification probability indicates that the holdout model classified the corresponding observation to have a particular lesion trait (e.g. in the benign class, malignant class or of a particular cancer subtype) with a corresponding probability. In a classification model that utilizes an ensemble of decision trees, the classification probability indicates the number of decision trees that generated a particular lesion trait out of the total number of decision trees.

The processors also build a second holdout model that is trained based on folds 1-8 and 10, while fold 9 represents the holdout fold that is not used to train the second holdout model. Instead, the observations in fold 9 are applied to the second holdout model to obtain 10 corresponding classification probabilities (referred to as estimate 2 or E2). The processors repeat the foregoing operation to build additional holdout models until each fold of the labeled data set has been utilized as a holdout fold and applied to a corresponding holdout model (built without using the holdout fold of observations). In the example of FIG. 3, 10 holdout folds are trained and then tested to obtain 10 estimates, where each estimate includes 10 classification probabilities from 10 corresponding observations.

Optionally, the data may be partitioned into more or fewer folds 304 which would yields an equal number of estimated models. The K estimates of performance are then averaged to give an aggregate estimate 314 with confidence intervals. Additionally or alternatively, the K-fold cross validation process can be repeated using different random number seeds to partition the folds. For example, repeated K-fold cross-validation can be used to evaluate the classification models (e.g., with 5 repeats and 10 folds for a total of 50 measurements).

For example, consider the example where a classification model includes an ensemble of 10 decision trees. OA feature scores and non-OA feature scores are applied to each of the 10 decision trees, in response to which, each decision tree outputs a single classification probability. For example, six of the decision trees may classify the observation, based on the OA and non-OA feature scores, to include a lesion trait in the malignant class, whereas the other four decision trees classify the observation to include a lesion trait in the benign class. In the foregoing example, the classification model would output a classification probability of 60% that the lesion trait is in the malignant class.

As an alternative example, the 10 decision trees of the classification model may include a decision trees that output eight classification probabilities indicating the lesion trait to be a first cancer subtype based on the OA and non-OA feature scores for the observation, whereas the remaining two decision trees output corresponding classification probabilities indicating that the lesion type is either in the benign class or another cancer subtype. In this alternative example, the classification model would output a classification probability of 80% that the lesion trait is in the first cancer subtype.

Returning to FIG. 3, for a labeled data set of 100 observations, each of the estimates 1-10 would include 10 classification probabilities of a particular lesion type for 10 corresponding observations, thereby yielding 100 classification probabilities from the group of 10 holdout models built for a labeled data set including 100 observations. As explained hereafter, the classification probabilities are utilized for further calculations.

Embodiments may utilize various evaluation metrics. Non-limiting examples of evaluation metrics include binary classifiers, metrics for accuracy, sensitivity, specificity, and area under the ROC (receiver operating characteristic) curve (AUC). The choice depends upon the class distribution and the intended use. Accuracy is a poor metric when the classes are imbalanced. AUC is appropriate if performance over all thresholds is relevant; however partial AUC (pAUC) is a better metric in cases where the focus is on a small region of the ROC curve, such as high sensitivity or high specificity.

The PML classifier is designed to assist in a biopsy/no biopsy decision where false negatives are associated with a heavy penalty. Therefore, embodiments utilize sensitivity and pAUC as the first metrics, with partial AUC computed over sensitivities from 95% to 100%. Sensitivity and specificity are dependent upon a threshold applied, which means that the threshold should be specified in order to evaluate and compare models. Current medical practice is to recommend a biopsy when the radiologist estimates the likelihood of cancer to be over 2%. Accordingly, the PML classification system and methods herein utilize a threshold that targets a 2% false negative rate (FNR). For example, if a test patient data set contains 500 observations for positive cases (i.e. patients having a malignant cancer) then the threshold is chosen such that the PML classification system and methods experience no more than 10 false negatives when predicting likelihood of malignancy based on the features of interest from the 500 observations. The final threshold for a classification model is the average threshold across the test patient data sets from the repeated K-fold cross-validation.

FIG. 5A illustrates a distributed operation diagram to further describe operations performed by a clinician computing device and a computing server in accordance with embodiments herein. The left side of the diagram represents operations performed by the clinician computing device, such as device 120 in FIG. 1, while the operations on the right side of the diagram are performed by the server, such as server 106. Beginning at 502, one or more processors of the computing device 120 obtain OA and US images. For example, the OA and US images may simply be read from a local or remote memory. Additionally or alternatively, the OA and US images may be obtained in real time, such as when the computing device 120 is connected to or is formed interval with an optoacoustic imaging system. At 504, the one or more processors of the computing device 120 assign OA and US features scores. For example, the OA and US features scores may be assigned by a human expert while viewing the OA and US images. Additionally or alternatively, the OA and US features scores may be automatically assigned by the processors based on automated segmentation and analysis of the OA and US images. The automated assignment of OA in US features may be performed entirely separate from, or in conjunction with, the viewing by the human expert. For example, the OA feature score may relate to one or more of the following OA features: 1) internal vascularity and de-oxygenation, 2) peri-tumoral boundary zone vascularity and deoxygenation, 3) internal deoxygenated blush, 4) internal total blood, 5) external peri-tumoral radiating vessels, and 6) interfering artifact. For example, the non-OA feature score may relate to one or more of the following ultrasound features: 1) US Shape Score, 2) US Internal Texture, 3) US Sound Transmission, 4) US Capsular or Boundary Zone, 5) US Peripheral Zone, 6) Patient Age, 7) Mammogram-BIRADS, 8) Lesion Size, and/or 9) Lesion Posterior Depth.

Next, optional operations at 506-508 are described. At 506, the computing device 120 generates a request for a list of available models that may be utilized. The request to be generated automatically, without user input, by the computing device 120. Optionally, the request may be generated in response to an instruction from the clinician through the GUI. The processors of the server 106 receive the request for the list of models and based thereon, identify the available models at 507. At 508, the processors of the server 106 return the list of available models to the computing device 120. The available models may be determined in various manners. For example, multiple ensembles of models may be stored in connection with one type of PML classifier. For example, the XGBTree PML classifier may generate multiple ensembles of models, where each ensemble of models is based on a different control labeled data set. Additionally or alternatively, each ensemble of models may be generated utilizing a different type of PML classifier. For example, the XGB tree PML classifier may generate a first ensemble of models utilizing a control labeled data set, while a logistic regression PML classifier may generate a second ensemble of models utilizing the same control labeled data set. Ensembles of models may be formed utilizing other types of PML classifiers.

Once the list of models is returned at 508, the computing device 120 selects one ensemble of models to be used in connection with the present individual patient. The selection of the ensemble of models may be performed manually by a clinician through the GUI. Additionally or alternatively, the processors of the computing device 120 may automatically select the ensemble of models based on various criteria. For example, the computing device 120 may automatically selecting ensemble of models based upon the amount of information available for the present individual patient, based upon a nature of the OA and US images and the like. Additionally or alternatively, when different cancer subtypes are separately modeled, a particular ensemble of models may be selected in connection with a particular subtype of cancer of interest. The operations at 506-508 are utilized when multiple ensembles of models are available. Optionally, when only a single ensemble of models is available, the operations at 506-508 may be omitted entirely.

At 510, the computing device 120 generates and sends an LOM request (more generally a predictive result request) to the server 106. The LOM request (predictive result request) may include, among other things, an identification of the ensemble of models to be utilized, as well as OA and US features scores and other patient specific data (e.g. age, Bi-RAD scores). The server 106 receives the OA and non-OA features scores in connection with OA images and non-OA images collected from a patient examination for a volume of interest, where the volume of interest includes a suspect lesion.

At 512, the processors of the server 106 apply the OA and non-OA features scores of the present observation to a designated master classification model and bootstrap classification models to obtain a predictive result indicative of a lesion trait (e.g. a likelihood that a lesion is in a malignant class or benign class). At 514, the processors of the server 106 obtain the classification probability based on the OA and non-OA features scores of the present observation as applied to the master classification model. Additionally or alternatively, the processors of the server 106 may obtain a positive predictive value, based on the PPV mapping function 402 (FIG. 4) and the current classification probability for the present observation. At 516, the processors of the server 106 obtain the prediction interval based on the OA and non-OA features scores of the present observation as applied to the bootstrap classification models.

At 518, the processors of the server 106 return, as a composite predictive result (PR) response the combination of the classification probability and/or PPV, and the reduction interval. As noted herein, the classification probability or the PPV may be utilized as the likelihood of malignancy. At 520, the processors of the computing device 120 output the composite PR (e.g. LOM and prediction interval), such as displaying the composite PR through the GUI 104. The output of the composite PR may also include storing the composite PR in connection with a patient's records. Additionally or alternatively, the computing device 120 may perform other actions based on the composite PR. For example, the computing device may send a notification to other medical personnel, initiate a report, initiate scheduling of a follow-up procedure and the like. As a further example, when the LOM and confidence interval indicate that a lesion is benign, the computing device 120 may send a notice or report automatically to the patient (e.g. via text message, email or other electronic notification means). Thereafter, the operations of FIG. 5A end.

Figure 5B:
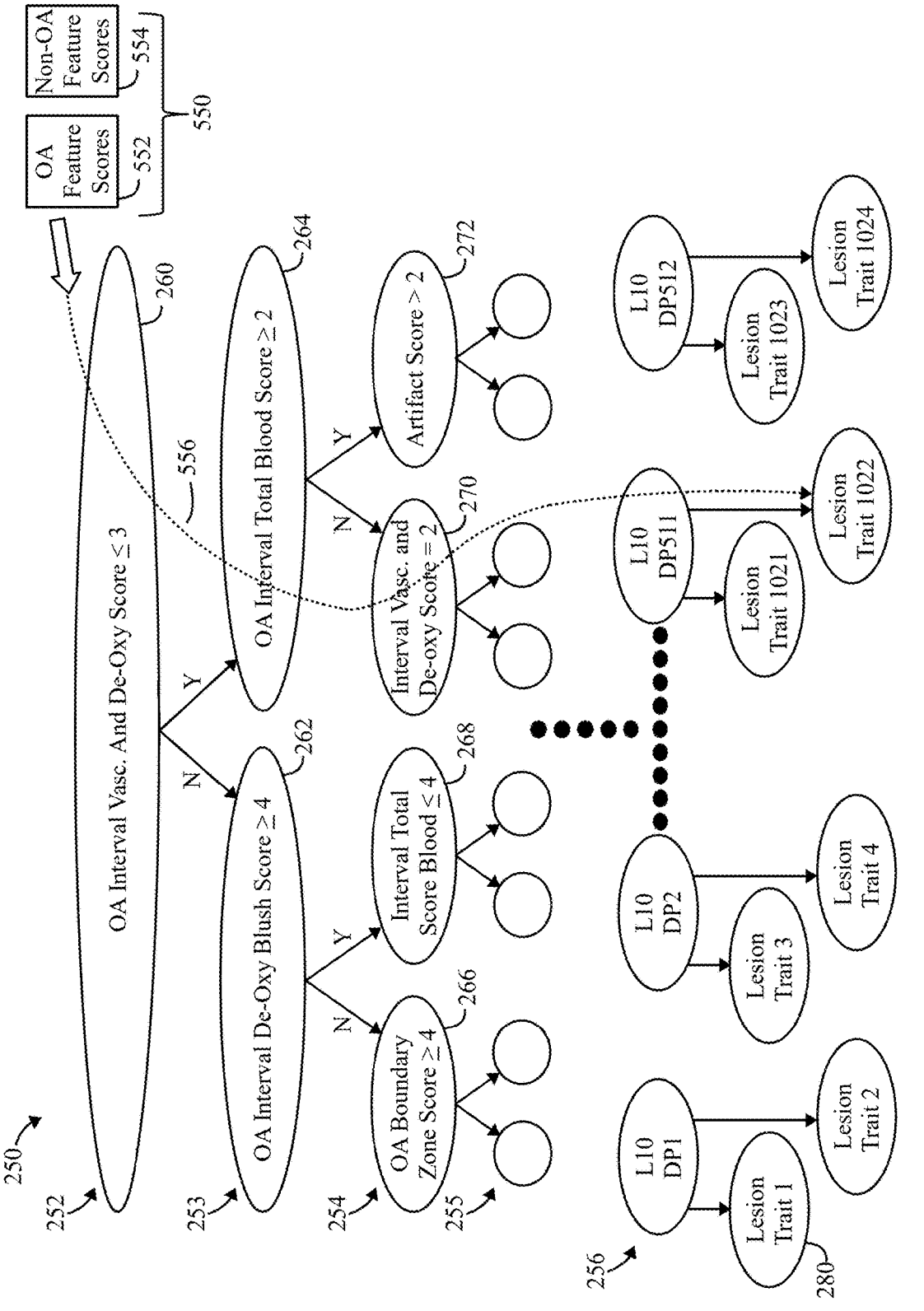
FIG. 5B illustrates a process for applying OA (and non-OA) feature scores to a classification model to obtain a lesion trait indicative of a likelihood that a lesion is in a malignant class or benign class in accordance with embodiments herein.

FIG. 5B illustrates a process for applying OA (and non-OA) feature scores to a classification model to obtain a lesion trait indicative of a likelihood that a lesion is in a malignant class or benign class in accordance with embodiments herein. The server 106 may utilize one or more processors to apply the OA and non-OA feature scores. The example of FIG. 5B illustrates, as the classification model, the decision tree 250 (described above in connection with FIG. 2B). The server 106 receives a request 550 from a clinician's computing device 120. One or more processors of the server 106 apply OA feature scores 552 and non-OA feature scores 554, from the request 550, to the decision tree

250. At 260, the processors determine whether the OA feature score for the internal vascularity and de-oxygenation is less than 3. In the example of FIG. 5B, the test is true and thus flow branches to decision point 264 as indicated by the dashed decision path 556. At 264, the processors determine whether the OA feature score for the internal total blood score is greater than or equal to 2. The test at 264 is faults and thus flow branches to decision point 270 where the processors determine whether the internal vascularity and de-oxygenation equals 2. The processors continue to test the OA and non-OA feature scores 252, 254 until reaching lesion trait 1022.

While the decision points in FIG. 5B only illustrate tests related to OA features, it is understood that the decision tree may also include decision points that test non-OA features, in order to apply a non-OA feature scores, in combination with OA feature scores, to the decision tree to obtain a lesion trait and/or a classification probability associated with the lesion trait.

While not illustrated, the processors of the server 106 apply the request 550 to the multiple decision trees of the master classification model, where each of the decision trees outputs a corresponding lesion trait. The processors of the server 106 combine the lesion traits obtained from the master classification model to obtain a classification probability. The classification probability may then be utilized as the likelihood of malignancy. Alternatively, the classification probability may be applied to the mapping function 402 (FIG. 4) to determine a corresponding positive predictive value that is then utilized as the likelihood of malignancy.

Additionally or alternatively, the processors of the server 16 may apply the request 550 to the decision trees of the bootstrapped models. Each of the bootstrapped models would return a classification probability for the current observation. The processors sort the classification probabilities into an ascending or descending order. The processors then select upper and lower limits for the prediction interval based on the target size of the prediction interval. For example, in a 90% prediction interval, the processors would select the classification probability at the 5% level as the lower limit of the prediction interval and the classification probability at the 95% level as the upper limit of the prediction interval. As a further example, if 100 bootstrapped models were trained and a current observation for a current patient were applied to the 100 bootstrapped models, 100 classification probabilities would be returned. The processors would sort the 100 classification probabilities into an ascending or descending order and then pick the fifth lowest and fifth highest classification probabilities to be the upper and lower limits of a 90% prediction interval. Alternatively, if a different prediction interval range (e.g. 80%) is desired, the processors would similarly pick the corresponding upper and lower classification probabilities (e.g. at the $10^{th}$ lowest and $10^{th}$ highest).

Optionally, the final layer of leaf nodes (corresponding to the lesion traits) may contain classification probabilities (e.g. the probability that the observation belongs to the malignant class). The classification probabilities at the leaf nodes may be computed when the tree is built. A partitioning process causes all observations in a training set to end up in one and only one leaf. The classification probability associated with a leaf node is the fraction of observations in the leaf that are labeled as malignant.

Figure 6:
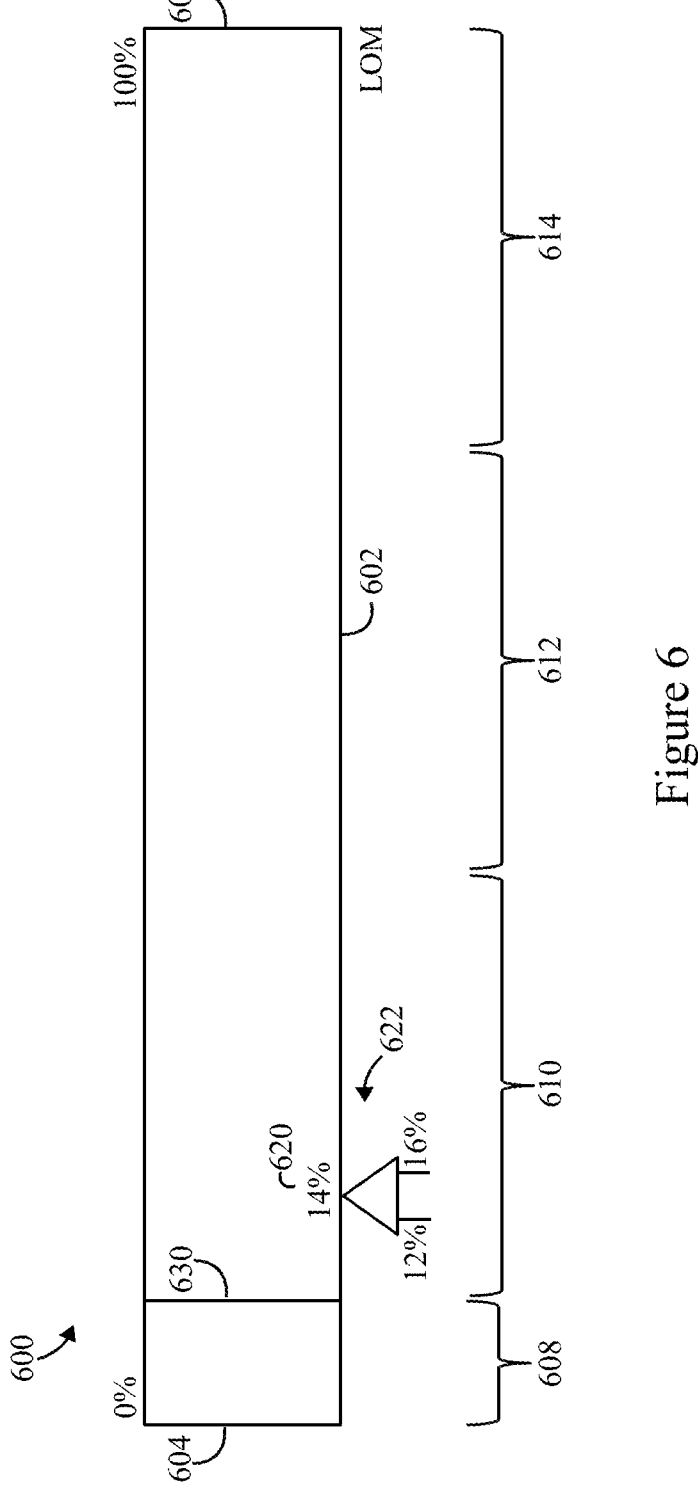
FIG. 6 illustrates an example of a manner in which a resultant predictive result may be displayed in accordance with embodiments herein.

FIG. 6 illustrates an example of a manner in which a resultant predictive result may be displayed in accordance with embodiments herein. The predictive result 600 may be presented along a color-coded scale 602, representing a likelihood of malignancy scale, where the scale extends from a 0% (e.g. 0% likelihood of malignancy) at a start 604 to 100% (e.g. 100% likelihood of malignancy) at an end 606. The color-coded scale 602 may include color shades that transition, such as between a green zone at 608, the yellow zone 610, and orange zone 612 and a red zone 614, where the colors merge between the zones. The predictive result 600 includes a LOM 620, which may correspond to the classification probability determined by the master composite model and/or the positive predictive value determined by the PPV mapping function 402. The predictive result 600 also includes a prediction interval 622 extending on either side of the LOM 620. In the present example, the prediction interval 622 extends between upper and lower limits at 14% to 16% likelihood that a lesion exhibits a particular trait (e.g. is in the malignant class).

Optionally, a decision threshold 630 may be provided on the color-coded scale 602, wherein the decision threshold 630 indicates a point at which a clinician may choose to make a care decision in which a patient obtains a biopsy from the lesion. For example, the decision threshold 630 may correspond to 98% sensitivity.

System and Method for Presenting Optoacoustic Data

Optoacoustic imaging (OA) is an imaging technique that uses pulsed laser light to illuminate the tissue, then resolves the optoacoustic waves generated by transient thermoelastic expansion following the absorption of the incident laser pulses by multiple absorbers such as hemoglobin, and deoxyhemoglobin. Optoacoustic systems using linear-array ultrasound (US) transducers leverage the advantage of using internal tissue contrast to add functional value to anatomical gray-scale US imaging. Prior clinical trials showed that when used as in combination with US, OA features of breast masses has the potential to help better differentiate malignant from benign masses, significantly decreasing false positive US assessments, with potential downstream effect of reducing unnecessary biopsies. In breast cancer, hypoxia mainly occurs because of the cancer's outgrowth of existing vasculature, and leads to adaptive responses that result in therapy response and tumor progression. The importance of hypoxia in breast tumor microenvironment as a significant indicator of poor prognosis has been well recognized in recent years. Imaging of hemoglobin concentration and its oxygenation status co-registered with the tumor image in real time may help better characterize breast cancers prognostically and assist clinical management decisions. Therefore, we undertook this study to investigate whether imaging-derived OA/US features correlate with breast cancer molecular subtypes determined by tissue immunohistochemistry.

Optoacoustic/ultrasound imaging systems as described below visualize thin tissue slices noninvasively through skin at a tissue site. The term "tissue site" broadly refers to locations or targets of animal and human tissues and organs such as, for example, breast tissue. A tissue site may contain a variety of different "tissue structures" that may include, for example, tumors, blood vessels, tissue layers, and components of blood. As described below, a sinogram may contain a sample recording of acoustic activity occurring over a period of time in response to one or more light events impinging on the tissue site. The acoustic activity captured in the sinogram may include an optoacoustic response, i.e., the acoustic signal that is created as a result of the electromagnetic energy being absorbed by materials within the tissue site such as, for example, various tissue structures that absorb the electromagnetic energy. These optical signals result from the release of thermo-elastic stress confinement within the tissue structures in response to the light events.

Figure 7:
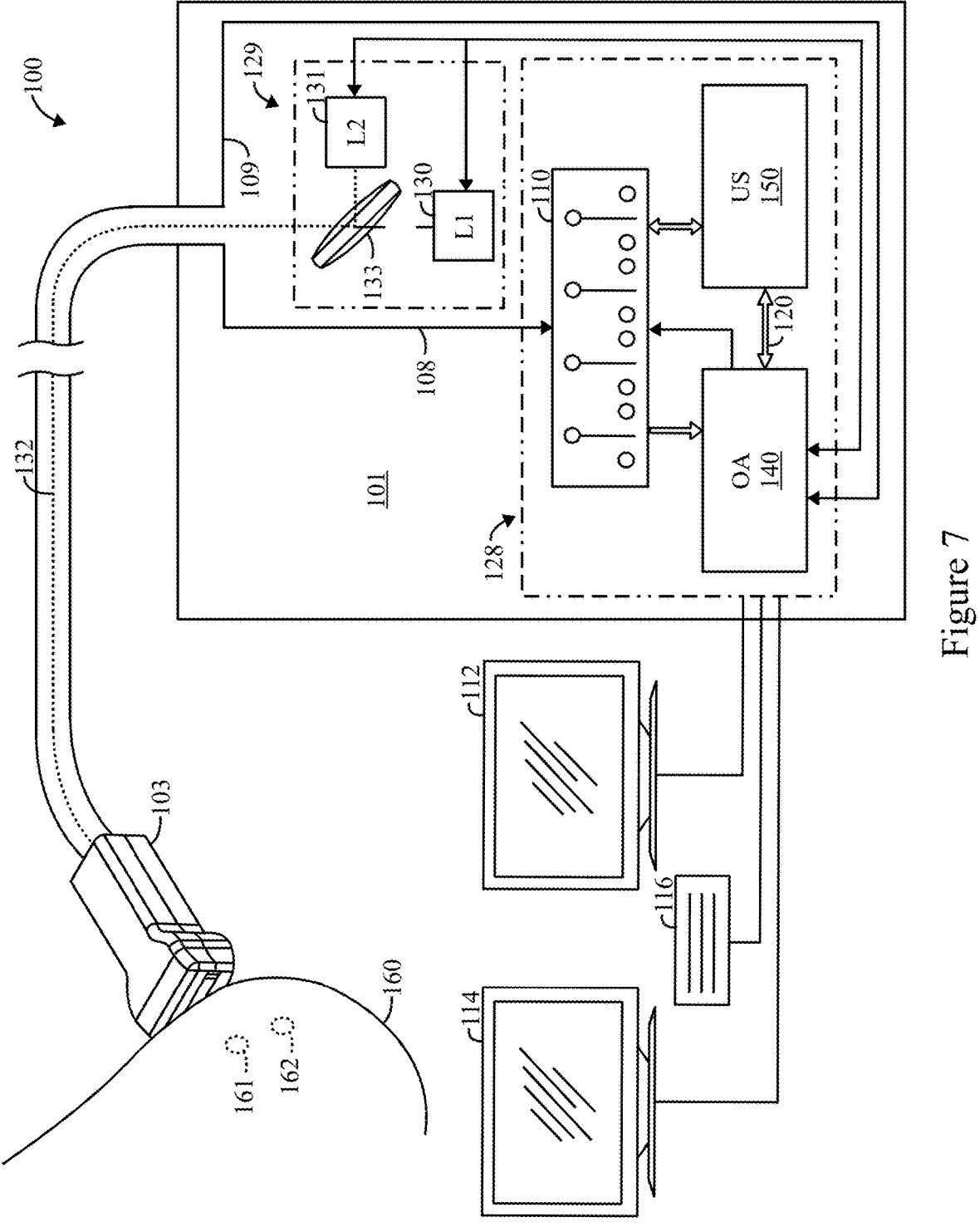
FIG. 7 illustrates a probe connected via a light path and an electrical path to a system chassis in accordance with embodiments herein.

Turning to FIG. 7, and as described generally below under the heading Optoacoustic System and Method is a device 100, including a probe 103 connected via a light path 132 and an electrical path 108 to a system chassis 101. Within the system chassis 101 is housed a light subsystem 129 and a computing subsystem 128. The computing subsystem 128 includes one or more computing components for, among other things, optoacoustic control and analysis. In an embodiment, through the sampling of transducers in the probe 103, the device 100 can obtain data received in response to: stimulation caused by pulsed light sources 130, 131 (i.e., the optoacoustic return signal); and to stimulation caused by acoustic output of the ultrasound transducer elements.

In an embodiment, to obtain an optoacoustic return signal corresponding to a single light event occurring in a volume of tissue, the transducers in the probe 103 can be sampled for a period of time after the light event. In an embodiment, the transducers in the probe 103 can be sampled for a period of time after the light event approximately equal to the time it would take sound to travel a desired distance in the tissue. In an embodiment, the desired distance may be at least one centimeter. In an embodiment, the desired distance may be at least two centimeters. In an embodiment, the period of sampling would correspond to the amount of time it would take sound to travel at least one, but not more than 15 centimeters in tissue. The sampling rate should be sufficient to obtain sufficient information in the optoacoustic return signal. In an embodiment, the sampling rate is above 20 megahertz (MHz), in another embodiment, the sampling rate is above about 30 MHz.

As discussed further below, in an embodiment, the device 100 comprises at least two light sources 130, 131 operating at different light wavelengths. In an embodiment, with two light sources 130, 131 operating at different light wavelengths, the optoacoustic return signal from one light event from each of the light sources can be used in the method and system for presenting the optoacoustic data. In an embodiment, the device 100 comprises a single light source that may be operated at different wavelengths, such as a tunable laser that can change wavelengths quickly enough for use as described herein. In an embodiment, the device 100 comprises at least two light sources 130, 131, each being capable of tuning to a plurality of different wavelengths. In an embodiment, the device 100 comprises one light source 130 operating a one light wavelength, and at least one additional light source 131 capable of being tuned to a plurality of different wavelengths.

As used herein, the term sinogram refers to sampled data or processed sampled data corresponding to a single light event. The term sinogram is also used at times to refer to an image presented by using the original or filtered sampled data as gray scale or color data, wherein there is a correspondence between the samples in the data and the voxels in the image. In an embodiment, using optoacoustic return signals from two different light events, each corresponding to a different wavelength of light, the term short sinogram refers to the sinogram corresponding to the shorter wavelength of light generating a light event, and the term long sinogram refers to the sinogram corresponding to the longer wavelength of light generating a light event. Because more than two different wavelengths may be used, the use of the terms short and long wavelength are intended to embody the extended context of a system with an arbitrary number of wavelengths.

In an embodiment, as discussed in more detail below, sinograms are processed to produce an envelope image. As used herein the term short envelope image refers to an envelope image corresponding to the short sinogram, and the term long envelope image refers to an envelope image corresponding to the long sinogram. In an embodiment, the short sinogram and long sinogram are each processed separately to produce a short envelope image and a long envelope image, respectively. The short and long envelope images are then used together to generate parametric images. From the parametric images, maps can be created of oxygenation, hemoglobin and masked oxygenation. These maps can be co-registered data representing an ultrasound image of substantially the same volume, and can thereafter produce one or more of an oxygenation image, a hemoglobin image and a masked oxygenation image. In an embodiment, the oxygenation image, hemoglobin image and masked oxygenation image reflect information about the composition of the volume of tissue. The terms parametric map and parametric image are in some instances used interchangeably. The use of the term map generally relates to the correspondence between the image and a volume. Parametric maps may be represented in numerous ways, including, for example, as a single-channel (i.e., grayscale) representation, as a color (i.e., RGB) representation, or as a color with transparency (RGBA) representation. Parametric maps may be used to convey qualitative or quantitative information about one or more parameters. A parametric map or parametric image may be represented in computer memory or presented as a displayed representation, thus, as used herein, the term "image" or "map" do not necessarily imply a visual representation.

For a variety of reasons, sinograms may contain unwanted, inaccurate or insufficiently scaled data. These maladies of sinogram data may result from myriad reasons, including characteristics of the measuring instrument (e.g., the probe) or the light used, characteristics of the volume (i.e., the tissue), characteristics of the interaction between the volume and the probe or light, external stimuli, or other sources. Regardless of the source, a variety of processes can be used to remove unwanted aspects of the sinogram data.

Generally in each of the following steps for processing the sinogram, the processing is performed on the time domain signal. In a preferred embodiment (and as discussed below) the probe 103 includes an acoustic lens that enables the sinogram data to be more focused on what is on the plane below that of the transducers-the image plane. In an embodiment, the probe comprises an acoustic lens having a focal length of between 10 and 40 millimeters. In an illustrative embodiment, the probe comprises an acoustic lens having a focal length of 20 millimeters. In an embodiment, the probe may comprise an acoustic lens having a focal length that can be zoomed in or out, in hardware, or in software.

As discussed above, in an illustrative embodiment, each channel of the sinogram data represents approximately 100 millimeters of distance in the volume. The acoustic lens generally rejects at least some portion of a signal propagating from points outside (e.g., orthogonal) to the image plane. Each transducer, however, receives signal from substantially all points of the image plane that lie within the approximately 100 millimeters distance. The received signal for a channel can be thought of as comprising the area of a semicircle of radius 100 millimeters on the image plane.

Figure 8:
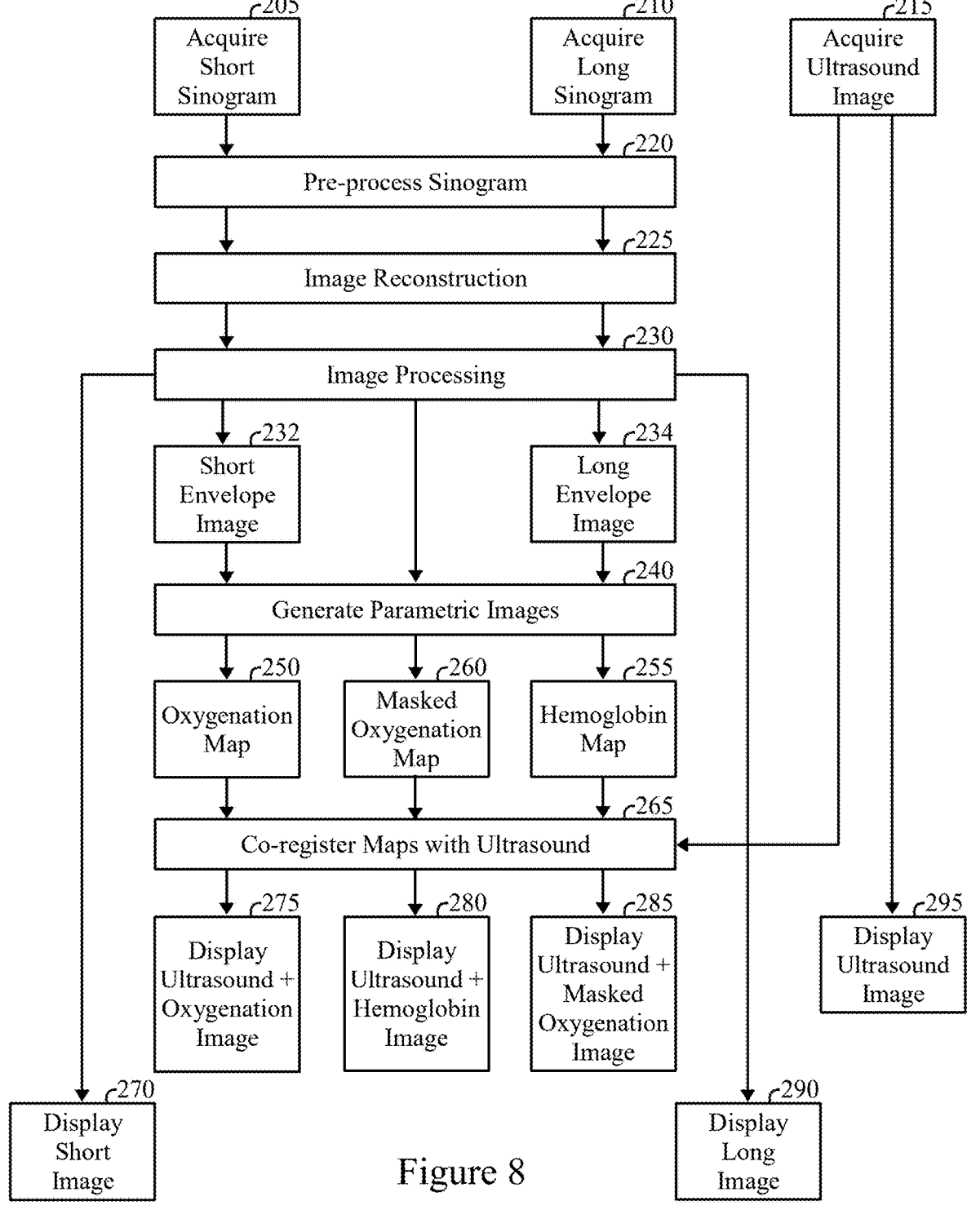
FIG. 8 illustrates a process in accordance with embodiments herein.

Turning to FIG. 8, an overview of an example process is shown, beginning with the acquisition of three sets of data, namely, a short sinogram (step 205), a long sinogram (step 210) and an ultrasound image (step 215), and processing the data to produce up to six separate images that may be useful in viewing various aspects of that acquired data. In an example embodiment, the three sets of acquired data may be acquired using a probe 103 (FIG. 7). For the purposes of illustration herein, it may be presumed that probe 103 movement is minimal, if any, between the acquisition of the three sets of data in steps 205, 210 and 215. In an example embodiment, a reasonable frame rate (e.g., 10 Hz), coupled with a reasonably steady hand used in handholding the probe may yield the three data sets having substantially minimal movement occurring there-between. It should be noted that the process described herein is not limited to being used with the three identified data sets. Use of additional data sets, such as, for example, data sets from additional wavelengths of light, may be used to further improve the resulting images.

As will be discussed in more detail below, the short and long sinogram data are preprocessed (step 220) in one or more separate manners to reduce or compensate for undesired data in the sinogram, including characteristics of the measuring instrument (e.g., the probe) or the light used, characteristics of the volume (i.e., the tissue), characteristics of the interaction between the volume and the probe or light, external stimuli, or other sources. After the preprocessing, separate short and long images are reconstructed (step 225). In an embodiment, separate real and imaginary components of complex short and long images result from the reconstruction step. In an embodiment, the processing (step 230) of the reconstructed images is performed. The processing (step 230) may remove additional artifacts that can be identified in the reconstructed images, and in any event creates a short envelope image (232) and a long envelope image (234). In an embodiment, the short and long envelope images (232, 234) are used to generate parametric images (step 240) process. The generated parametric images (step 240) process outputs an oxygenation map (250), a hemoglobin map (255) and a masked oxygenation map (260). In an embodiment, any or all of the three maps are co-registered with, and overlaid on an ultrasound image (step 265). A display can be provided for display of one or more of the displayable images displayed in steps 270, 275, 280, 285, 290 and 295. In an embodiment, a group of two or more of the images may be displayed on the same screen, and may be commonly scaled and sized. In an embodiment, the group of all six images may be displayed on the same screen, and may be commonly scaled and sized.

In an embodiment, the system performing processing on the optoacoustic data, and/or the system displaying the optoacoustic output-which may, but need not be the same as the system acquiring the sinogram-would provide the operator the ability to vary parameters used in processing, when processing or viewing optoacoustic images. In an embodiment, the system performing processing on the optoacoustic data, and/or the system displaying the optoacoustic output would provide the operator the ability to switch on and off, and potentially vary the order of, the processing steps used to process the optoacoustic images.

Returning to FIG. 7, generally, device 100 provides an optoacoustic system that may also be employed as multi-modality, combined optoacoustic and ultrasound system. In an embodiment, the device 100 includes a probe 103 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, an optoacoustic processing and overlay system 140 and an ultrasound instrument 150.

In an embodiment, the light subsystem 129 is capable of producing pulses of light of at least two different wavelengths. In an embodiment, the light subsystem 129 outputs should be capable of producing short pulses of light in each of those wavelengths, e.g., a pulse lasting less than about 100 ns, and potentially as short as about 5 ns. As will be apparent to one of ordinary skill in the art from this disclosure, the inventions disclosed herein may also be practiced using pulsed light comprising pulses lasting greater than 100 ns. In an embodiment, the light subsystem 129 includes two separate light sources 130, 131. The output of the light subsystem 129 is delivered to the probe 103 via the light path 132. In an embodiment, the light sources 130, 131 are lasers producing light in the infrared, near-infrared, and/or visible spectrum. In an embodiment, light source 130 and light source 131 each produce light at a different wavelength in the infrared or near-infrared spectrum. In an embodiment, the light path 132 used to deliver light from the light subsystem 129 to the probe 103 is a fiber optic bundle comprising multiple strands of optical fiber. In an embodiment, the light path 132 comprises sufficient optical fibers of sufficient size (diameter) to carry a short, high powered pulse of light to the distal end of the light path 132. In an embodiment, the total pulse energy carried over the light path 132 may be on the order of one or more millijoules. In an embodiment, the total energy per light pulse delivered from the light path 132 is less than about 100 millijoules. In an embodiment, the total energy per light pulse carried over the light path 132 is in the range of about 50-90 millijoules, and the light path 132 comprises between about 1,000 and 2,000 optical fibers of between about 100 and 300 microns each. In an embodiment, a single fiber can be used as the light path 132. In such embodiment, the fiber may be 1000-1500 microns in diameter. Of course, the diameter of such single fiber may be smaller, e.g., 400 microns. Given the required total pulse energy carried over the fiber, one skilled in the art can calculate the diameter required of the fiber accordingly.

In an illustrative embodiment, the light subsystem 129 may use Nd:YAG and Alexandrite lasers as its two light sources 130, 131, although other types or wavelengths, and additional lights, may also be used. Light sources 130, 131 should be capable of producing a short pulse of light, e.g., a pulse lasting less than about 100 ns, and more preferably around 5 ns. In an embodiment, the two light sources 130, 131 can be separately triggered. In an embodiment, the light output by the light sources 130, 131 may be projected onto the same light path 132 through the use of an optical element 133 that generally permits one light 130 to pass through from a first side to a second side, while reflecting one light source 131 that strikes the second side. The use of optical element 133 or a similar element permits the alignment of the output of two light sources 130, 131 such as lasers onto proximal end of the light path 132. In an embodiment, optical elements 133 can align the light output from more than two lasers, for example, through the use of multiple optical elements 133. In an embodiment, multiple light systems and light paths may be employed, with the light of each light system being carried on separate fibers or fiber groups that may be intermingled and/or randomized (discussed further below) and/or grouped at their distal ends. Intermingled, as used in this context, refers to the mapping of the fibers in the light path such that fibers are generally distributed in a relatively even manner in the distal groupings. Thus, a plurality of adjacent fibers on the proximal end of the light path would generally be about evenly divided in groupings on the distal end. As an illustrative example, where there are two distal groupings, any arbitrary selection of a sufficient group of adjacent fibers on the proximal end should be about evenly split between the two distal groupings. The randomization, intermingling and/or grouping need not take place at any specific location on the light path 132. In other words, for example, the division of a fiber cable from one proximal group to two distal groups can occur at any point along the light path 132, or along substantially the entire length of the light path 132. Similarly, the randomization and/or intermingling need not take place along the entire length of the light path, but rather, for example, may take along a the distance of, e.g., a few centimeters or more near either end of the light path, or anywhere else along the light path 132. Randomizing fibers between one end and the other end of a light path prevents a local anomaly affecting an adjacent group of the fibers on the input from affecting a significant adjacent group of the fibers on the output. Intermingling fibers between one end and the other end of a light path prevents a local anomaly affecting an adjacent group of the fibers on the input from disproportionately affecting one group or subgroup of fibers on the output.

Where the light path terminates in multiple groupings (or subgroupings) of fibers, the distal ends of the groupings (or subgroupings) may be fused, or lapped and polished, or just secured together (removable or otherwise). In an embodiment, the distal end of the light path is formed into a plurality of groups that are spaced in such a manner so as to permit light to emit on each side of the transducer array. In an embodiment, the distal end of the light path is formed into a plurality of groups that are spaced in such a manner so as to permit light to emit around the entire transducer array. In an embodiment, the distal end of the light path is formed into two or more groups, and the two or more groups subdivided into subgroups that are separately secured by a light bar guide, which light bar guide may be associated with the group. In an embodiment, optical elements 133 can consist of optical elements that are used to measure the light energy to determine energy per light pulse.

Although the total energy per light pulse carried over the light path 132 is in the order of tens of millijoules, because the pulse of light sources 130, 131 is so short, the peak power output over the light path 132 is frequently approaching or in the megawatt range. Accordingly, the output of light sources 130, 131 has the capacity to cause the optical fibers and/or the cladding on the optical fibers to burn, discolor or otherwise degrade. Such degraded optical fibers and/or cladding, whether burnt, discolored, or otherwise, can exacerbate the problem as they begin to transmit less light power and cause more heating. Accordingly, in an embodiment, sufficient number and size optical fibers are present in the light path 132 to permit handling of the peak power loads and avoid fiber burnout. To accommodate higher peak power, a larger fiber bundle can be used. It will be apparent to a person of skill in the art that the peak power capacity of a fiber bundle can be increased by increasing the number of optical fibers, or the diameter of optical fibers, or both. Notably, however, as the dimension of the fiber bundle increases, the weight and flexibility of the light path 132 may become less desirable. Moreover, when using more optical fibers, or optical fibers of a larger diameter, the output of light subsystem 129 must be delivered to the light path 132 across the wider diameter of the larger bundle. In an embodiment, regardless of the ultimate size of the proximal end of light path 132, the output of light subsystem 129 should be distributed sufficiently across its cross section to prevent burn out failures when operating in expected peak power ranges.

In an embodiment, the fibers of the proximal end of the light path 132 may be fused to form a fused entry point to the light path 132 for the output of light subsystem 129. In an embodiment, the fiber ends can be fused by applying heat. In an embodiment, a fused end may be surrounded with a metal ring. In an embodiment, a fused end may be surrounded with a stainless steel ring. Once the proximal end of light path 132 has been fused, it will resist burnout at substantially higher peak power. For example, using a fused end light path 132 may permit carriage of three, four or even five times as much peak power. The ability to carry substantially higher peak power in a given light path 132 permits use of a more flexible and lighter fiber optic bundle to carry the same peak power as an un-fused light path 132. Thus, in an embodiment, where a ½" (12.7 mm) fiber optic bundle may have been required in an un-fused bundle of optical fibers forming a light path, a ¼" (6.35 mm) fiber optic bundle with a fused proximal end may be used to carry the same peak power. A ¼" (6.35 mm) fiber optic bundle with a fused proximal end is approximately ¼ of the weight and much more flexible than a ½" (12.7 mm) fiber optic bundle. Moreover, fusing of the proximal end of light path 132 may produce an even smaller fused area to illuminate using light source 132 as the fusing removes the inter-fiber spaces that would have existed in the bundled end of the round-cross-section optical fibers. Accordingly, one or more of the following advantages may be attained by fusing the proximal end of the optical fibers comprising the light path 132: reduced weight of the light path; increased flexibility of the light path; reduced failure; increased reliability; higher peak power capacity.

In an embodiment, the proximal end of the light path 132 may be separated into separate groups for separate light sources 130, 131 in a light source 132, and light output by the light sources 130, 131 may be projected onto different proximal groups of the light path 132. More than two separate lights may be used, and the proximal end of the light path 132 may be separated into at least one group for each light. Each group of fibers at the proximal end of the light path 132 may be fused together to form a fused entry point to the light path 132 for the light with which it is associated. In an embodiment, the fibers of a light path having multiple groups on the proximal and are intermingled with respect to the groups or subgroups on the proximal ends. In an embodiment, the fibers of a light path having multiple groups on the proximal and are randomized with respect to the groups or subgroups on the proximal ends. In an embodiment, a light path is provided with a fused proximal end (input) and at least two groups on its distal end (outputs), the fibers being intermingled and randomized, thus preventing a local anomaly affecting adjacent fibers at the input of the light path from: (i) causing an anomaly affecting a substantial number of adjacent fibers on an output; and (ii) disproportionately affecting one of the outputs. In an embodiment, a light path is provided with at least two groups on its proximal end (inputs) and at least two groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs. In an embodiment, a light path is provided with at least two fused groups on its proximal end (inputs) and at least two fused groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs.

In an embodiment, optical fiber of the type that may be used in light path 132 includes a transparent core surrounded by a transparent cladding material with a lower index of refraction. The core may be made from any transparent material, although excellent results have been observed using pure glass (i.e., silica). In an embodiment, where a bundle of optical fibers are to be fused, the cladding may be removed in the area to be fused. In an embodiment, the cladding may be removed using a chemical process. For example, for some cladding, hot sulfuric acid or acetone may be used. The removal of cladding prior to fusing reduces the chance of particles of the cladding material becoming embedded in the fused end; as such particles may interfere with the light transmission across light path 132.

In an embodiment, the light output by the light sources 130, 131 is sent towards a fused optical fiber bundle at the proximal end of light path 132 via a light path, which may include optical element 133, internal to the light subsystem 129. In an embodiment, light subsystem 129 is a laser system capable of outputting laser light pulses, at one or more wavelengths, onto light path 132. In an embodiment, light path 132 is a fiber optic bundle having a fused end proximal to the light subsystem 129.

In an embodiment, the device 100 also comprises an electrical path 108 running to and/or from the probe 103 to the system chassis 101. In an embodiment, electrical path 108 runs to and/or from the probe 103 to a relay system 110 within the system chassis 101. The electrical path 108 may run near, alongside or coaxially with the light path 132 from the probe 103 toward their respective connections on the system chassis 101. In an embodiment, the electrical path 108 comprises a plurality of separate coaxial wires. In an embodiment, the electrical path 108 is run in a common jacket with at least a portion of the light path 132. Running electrical path 108 in a common jacket with at least a portion of the light path 132 reduces the number of cables running from the system chassis 101 to the probe 103. Running electrical path 108 in a common jacket with at least a portion of the light path 132 may minimize the diameter and weight of, and increase the durability of, the combined cables (i.e., light path 132 and electrical path 108) running from the system chassis 101 to the probe 103.

One or more displays 112, 114, which may be touch screen displays, are provided for displaying images and all or portions of the device 100 user interface. One or more other user input devices (not shown) such as a keyboard, mouse and various other input devices (e.g., dials and switches) may be provided for receiving input from an operator. As an option, power and control path(s) 109 carry power to the probe 103 and control signals between the probe 103 and the computing subsystem 128.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc.

Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

The invention claimed is:

1. A method, comprising:
utilizing one or more processors for, receiving a labeled data set for multiple patients, the labeled data set including optoacoustic (OA) feature scores for lesions in OA images of volumes of interest from examinations for the multiple patients, the labeled data set including class designators indicating a trait of the lesion; and
building an ensemble of classification models, associated with OA classification prediction, based on the OA feature scores and the class designators in the labeled data set, wherein each of the classification models include predictive results indicative of the trait of the lesion, each of the classification models built utilizing a predictive machine learning (PML) classifier.

2. The method of claim 1, wherein the labeled data set includes a combination of i) the OA feature scores for OA images from examinations of the multiple patients ii) the class designator that has been determined and recorded with the OA feature scores, and iii) non-OA feature scores for non-OA images from examinations of the multiple patient, the ensemble of classification models built based on the OA feature scores, the class designators and the non-OA feature scores.

3. The method of claim 1, wherein the PML classifier includes one or more of classification and regression trees (CART), C4.5 decision trees, K nearest-neighbor, Support Vector Machines (SVM), and Naïve Bayes classifiers.

4. The method of claim 1, wherein the PML classifier utilizes a random forest algorithm to build an ensemble of decision trees corresponding to the ensemble of classification models.

5. The method of claim 1, wherein the PML classifier utilizes an extreme gradient boosting algorithm to build the ensemble of classification models.

6. The method of claim 5, wherein the extreme gradient boosting algorithm is used in combination with classification and regression trees (CART) decision trees to build the ensemble of classification models.

7. The method of claim 1, wherein the classification models represent decision trees that comprise decision points, branches and lesion traits.

8. A system, comprising:
memory configured to store program instructions;
one or more processors that, when executing the program instructions, are configured to:
receive a labeled data set for multiple patients, the labeled data set including OA feature scores for lesions in OA images of volumes of interest from examinations for the multiple patients, the labeled data set including class designators indicating whether the lesions are in a benign class or malignant class; and
build an ensemble of classification models, associated with OA classification prediction, based on the OA feature scores and the class designators in the labeled data set, wherein each of the classification models include predictive results indicative of the trait of the lesion, each of the classification models built utilizing a predictive machine learning (PML) classifier.

9. The system of claim 8, wherein the labeled data set includes a combination of i) the OA feature scores for OA images from examinations of the multiple patients ii) the class designator that has been determined and recorded with the OA feature scores, and iii) non-OA feature scores for non-OA images from examinations of the multiple patient, the ensemble of classification models built based on the OA feature scores, the class designators and the non-OA feature scores.

10. The system of claim 8, wherein the PML classifier includes one or more of classification and regression trees (CART), C4.5 decision trees, K nearest-neighbor, Support Vector Machines (SVM), and Naïve Bayes classifiers.

11. The system of claim 8, wherein the PML classifier utilizes a random forest algorithm to build an ensemble of decision trees corresponding to the classification models.

12. The system of claim 8, wherein the PML classifier utilizes an extreme gradient boosting algorithm to build the ensemble of classification models.

13. The system of claim 12, wherein the extreme gradient boosting algorithm is used in combination with classification and regression trees (CART) decision trees to build the classification models.

14. The system of claim 8, wherein the classification models represent decision trees that comprise decision points, branches and lesion traits.

\* \* \* \* \*